(12) United States Patent
Hon et al.

(10) Patent No.: US 11,935,628 B2
(45) Date of Patent: Mar. 19, 2024

(54) FINDING RELATIVES IN A DATABASE

(71) Applicant: 23andMe, Inc., Sunnyvale, CA (US)

(72) Inventors: Lawrence Hon, Sunnyvale, CA (US); Serge Saxonov, Oakland, CA (US); Brian Thomas Naughton, Mountain View, CA (US); Joanna Louise Mountain, Menlo Park, CA (US); Anne Wojcicki, Palo Alto, CA (US); Linda Avey, Lafayette, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

(21) Appl. No.: 17/979,412

(22) Filed: Nov. 2, 2022

(65) Prior Publication Data

US 2023/0298704 A1    Sep. 21, 2023

Related U.S. Application Data

(63) Continuation of application No. 17/576,738, filed on Jan. 14, 2022, now Pat. No. 11,508,461, which is a
(Continued)

(51) Int. Cl.
*G06F 16/00* (2019.01)
*G06F 16/2457* (2019.01)
(Continued)

(52) U.S. Cl.
CPC ......... *G16B 50/30* (2019.02); *G06F 16/2457* (2019.01); *G06F 16/9535* (2019.01);
(Continued)

(58) Field of Classification Search
None
See application file for complete search history.

(56) References Cited

U.S. PATENT DOCUMENTS

| 5,288,644 A | 2/1994 | Beavis |
| 5,301,105 A | 4/1994 | Cummings, Jr. |
(Continued)

FOREIGN PATENT DOCUMENTS

| EP | 0967291 A1 | 12/1999 |
| WO | 1990015070 A1 | 12/1990 |
(Continued)

OTHER PUBLICATIONS

Traherne. PLOS Genetics. "Genetic analysis of completely sequenced disease-associated MHC haplotypes identifies shuffling of segments in recent human history." Jan. 2006 (Year: 2006).*
(Continued)

*Primary Examiner* — Tuankhanh D Phan
(74) *Attorney, Agent, or Firm* — McDonnell Boehnen Hulbert & Berghoff LLP; David K. Buckingham

(57) ABSTRACT

Determining relative relationships of people who share a common ancestor within at least a threshold number of generations includes: receiving recombinable deoxyribonucleic acid (DNA) sequence information of a first user and recombinable DNA sequence information of a plurality of users; processing, using one or more computer processors, the recombinable DNA sequence information of the plurality of users in parallel; determining, based at least in part on a result of processing the recombinable DNA information of the plurality of users in parallel, a predicted degree of relationship between the first user and a user among the plurality of users, the predicted degree of relative relationship corresponding to a number of generations within which the first user and the second user share a common ancestor.

20 Claims, 15 Drawing Sheets

Related U.S. Application Data continuation of application No. 17/351,052, filed on Jun. 17, 2021, now Pat. No. 11,322,227, which is a continuation of application No. 17/073,110, filed on Oct. 16, 2020, now Pat. No. 11,049,589, which is a continuation of application No. 16/129,645, filed on Sep. 12, 2018, now abandoned, which is a continuation of application No. 15/264,493, filed on Sep. 13, 2016, now abandoned, which is a continuation of application No. 13/871,744, filed on Apr. 26, 2013, now abandoned, which is a continuation of application No. 12/644,791, filed on Dec. 22, 2009, now Pat. No. 8,463,554.

(60) Provisional application No. 61/204,195, filed on Dec. 31, 2008.

(51) Int. Cl.
  G06F 16/9535 (2019.01)
  G06N 5/048 (2023.01)
  G16B 10/00 (2019.01)
  G16B 30/00 (2019.01)
  G16B 50/00 (2019.01)
  G16B 50/30 (2019.01)

(52) U.S. Cl.
  CPC ............ *G06N 5/048* (2013.01); *G16B 10/00* (2019.02); *G16B 30/00* (2019.02); *G16B 50/00* (2019.02)

(56) References Cited

U.S. PATENT DOCUMENTS

| | | |
|---|---|---|
| 5,376,526 A | 12/1994 | Brown |
| 5,384,261 A | 1/1995 | Winkler |
| 5,424,186 A | 6/1995 | Fodor |
| 5,446,886 A | 8/1995 | Li |
| 5,551,880 A | 9/1996 | Bonnstetter |
| 5,649,181 A | 7/1997 | French |
| 5,660,176 A | 8/1997 | Iliff |
| 5,692,501 A | 12/1997 | Minturn |
| 5,752,242 A | 5/1998 | Havens |
| 5,769,074 A | 6/1998 | Barnhill |
| 5,839,120 A | 11/1998 | Thearling |
| 5,940,802 A | 8/1999 | Hildebrand |
| 5,985,559 A | 11/1999 | Brown |
| 6,014,631 A | 1/2000 | Teagarden |
| 6,063,028 A | 5/2000 | Luciano |
| 6,108,647 A | 8/2000 | Poosala |
| 6,131,092 A | 10/2000 | Masand |
| 6,203,993 B1 | 3/2001 | Shuber |
| 6,216,134 B1 | 4/2001 | Heckerman |
| 6,253,203 B1 | 6/2001 | O'Flaherty |
| 6,269,364 B1 | 7/2001 | Kennedy |
| 6,321,163 B1 | 11/2001 | Graham |
| 6,393,399 B1 | 5/2002 | Even |
| 6,450,956 B1 | 9/2002 | Rappaport |
| 6,487,541 B1 | 11/2002 | Aggarwal |
| 6,493,637 B1 | 12/2002 | Steeg |
| 6,506,562 B1 | 1/2003 | Weissman |
| 6,507,840 B1 | 1/2003 | Joannidis |
| 6,519,604 B1 | 2/2003 | Acharya |
| 6,601,059 B1 | 7/2003 | Fries |
| 6,629,097 B1 | 9/2003 | Keith |
| 6,629,935 B1 | 10/2003 | Miller |
| 6,640,211 B1 | 10/2003 | Holden |
| 6,687,696 B2 | 2/2004 | Hofmann |
| 6,694,311 B1 | 2/2004 | Smith |
| 6,703,228 B1 | 3/2004 | Landers |
| 6,730,023 B1 | 5/2004 | Dodds |
| 6,738,762 B1 | 5/2004 | Chen |
| 6,873,914 B2 | 3/2005 | Winfield |
| 6,887,666 B1 | 5/2005 | Hager |
| 6,912,492 B1 | 6/2005 | Johnson |
| 6,931,326 B1 | 8/2005 | Judson |
| 6,994,962 B1 | 2/2006 | Thilly |
| 7,054,758 B2 | 5/2006 | Gill-Garrison |
| 7,062,752 B2 | 6/2006 | Simpson |
| 7,069,308 B2 | 6/2006 | Abrams |
| 7,072,794 B2 | 7/2006 | Wittkowski |
| 7,076,504 B1 | 7/2006 | Handel |
| 7,107,155 B2 | 9/2006 | Frudakis |
| 7,127,355 B2 | 10/2006 | Cox |
| 7,162,471 B1 | 1/2007 | Knight |
| 7,271,243 B2 | 9/2007 | Dumas Milne Edwards |
| 7,292,944 B2 | 11/2007 | Larder |
| 7,366,719 B2 | 4/2008 | Shaw |
| 7,461,006 B2 | 12/2008 | Gogolak |
| 7,461,077 B1 | 12/2008 | Greenwood |
| 7,567,870 B1 | 7/2009 | Hood |
| 7,572,603 B2 | 8/2009 | Small |
| 7,592,910 B2 | 9/2009 | Tuck |
| 7,630,986 B1 | 12/2009 | Herz |
| 7,720,855 B2 | 5/2010 | Brown |
| 7,739,247 B2 | 6/2010 | Mount |
| 7,752,215 B2 | 7/2010 | Dettinger |
| 7,783,665 B1 | 8/2010 | Tormasov |
| 7,788,358 B2 | 8/2010 | Martino |
| 7,797,302 B2 | 9/2010 | Kenedy |
| 7,818,310 B2 | 10/2010 | Kenedy |
| 7,818,396 B2 | 10/2010 | Dolin |
| 7,844,609 B2 | 11/2010 | Kenedy |
| 7,877,398 B2 | 1/2011 | Kroeschel |
| 7,904,511 B2 | 3/2011 | Ryan |
| 7,917,374 B2 | 3/2011 | Walker |
| 7,917,438 B2 | 3/2011 | Kenedy |
| 7,930,156 B2 | 4/2011 | Maruhashi |
| 7,933,912 B2 | 4/2011 | Kenedy |
| 7,941,329 B2 | 5/2011 | Kenedy |
| 7,941,434 B2 | 5/2011 | Kenedy |
| 7,951,078 B2 | 5/2011 | Scheuner |
| 7,957,907 B2 | 6/2011 | Sorenson |
| 7,996,157 B2 | 8/2011 | Zabeau |
| 8,024,348 B2 | 9/2011 | Kenedy |
| 8,051,033 B2 | 11/2011 | Kenedy |
| 8,055,643 B2 | 11/2011 | Kenedy |
| 8,065,324 B2 | 11/2011 | Kenedy |
| 8,073,708 B1 | 12/2011 | Igoe |
| 8,099,424 B2 | 1/2012 | Kenedy |
| 8,108,406 B2 | 1/2012 | Kenedy |
| 8,156,158 B2 | 4/2012 | Rolls |
| 8,185,461 B2 | 5/2012 | Kenedy |
| 8,187,811 B2 | 5/2012 | Eriksson |
| 8,200,509 B2 | 6/2012 | Kenedy |
| 8,209,319 B2 | 6/2012 | Kenedy |
| 8,224,835 B2 | 7/2012 | Kenedy |
| 8,255,403 B2 | 8/2012 | Kenedy |
| 8,326,648 B2 | 12/2012 | Kenedy |
| 8,335,652 B2 | 12/2012 | Soykan |
| 8,386,519 B2 | 2/2013 | Kenedy |
| 8,428,886 B2 | 4/2013 | Wong |
| 8,452,619 B2 | 5/2013 | Kenedy |
| 8,458,097 B2 | 6/2013 | Kenedy |
| 8,458,121 B2 | 6/2013 | Kenedy |
| 8,463,554 B2 | 6/2013 | Hon |
| 8,510,057 B1 | 8/2013 | Avey |
| 8,543,339 B2 | 9/2013 | Wojcicki |
| 8,589,437 B1 | 11/2013 | Khomenko |
| 8,606,761 B2 | 12/2013 | Kenedy |
| 8,635,087 B1 | 1/2014 | Igoe |
| 8,645,343 B2 | 2/2014 | Wong |
| 8,655,821 B2 | 2/2014 | Aliferis |
| 8,655,899 B2 | 2/2014 | Kenedy |
| 8,655,908 B2 | 2/2014 | Kenedy |
| 8,655,915 B2 | 2/2014 | Kenedy |
| 8,719,045 B2 | 5/2014 | Yoon |
| 8,738,297 B2 | 5/2014 | Sorenson |
| 8,744,982 B2 | 6/2014 | Crockett |
| 8,786,603 B2 | 7/2014 | Rasmussen |
| 8,788,283 B2 | 7/2014 | Kenedy |
| 8,788,286 B2 | 7/2014 | Kenedy |
| 8,855,935 B2 | 10/2014 | Myres |

(56) References Cited

U.S. PATENT DOCUMENTS

| | | |
|---|---|---|
| 8,898,021 B2 | 11/2014 | Perlin |
| 8,990,198 B2 | 3/2015 | Rolls |
| 8,990,250 B1 | 3/2015 | Chowdry |
| 9,031,870 B2 | 5/2015 | Kenedy |
| 9,092,391 B2 | 7/2015 | Stephan |
| 9,116,882 B1 | 8/2015 | Macpherson |
| 9,170,992 B2 | 10/2015 | Kenedy |
| 9,213,944 B1 | 12/2015 | Do |
| 9,213,947 B1 | 12/2015 | Do |
| 9,218,451 B2 | 12/2015 | Wong |
| 9,336,177 B2 | 5/2016 | Hawthorne |
| 9,367,663 B2 | 6/2016 | Deciu |
| 9,367,800 B1 | 6/2016 | Do |
| 9,390,225 B2 | 7/2016 | Barber |
| 9,405,818 B2 | 8/2016 | Chowdry |
| 9,486,429 B2 | 11/2016 | Summar |
| 9,582,647 B2 | 2/2017 | Kenedy |
| 9,836,576 B1 | 12/2017 | Do |
| 9,864,835 B2 | 1/2018 | Avey |
| 9,928,338 B2 | 3/2018 | Tang |
| 9,977,708 B1 | 5/2018 | Do |
| 9,984,198 B2 | 5/2018 | Deciu |
| 10,025,877 B2 | 7/2018 | Macpherson |
| 10,162,880 B1 | 12/2018 | Chowdry |
| 10,275,569 B2 | 4/2019 | Avey |
| 10,296,842 B2 | 5/2019 | Lu |
| 10,296,847 B1 | 5/2019 | Do |
| 10,379,812 B2 | 8/2019 | Kenedy |
| 10,432,640 B1 | 10/2019 | Hawthorne |
| 10,437,858 B2 | 10/2019 | Naughton |
| 10,468,141 B1 | 11/2019 | Valenzuela |
| 10,516,670 B2 | 12/2019 | Hawthorne |
| 10,572,831 B1 | 2/2020 | Do |
| 10,643,740 B2 | 5/2020 | Avey |
| 10,658,071 B2 | 5/2020 | Do |
| 10,691,725 B2 | 6/2020 | Naughton |
| 10,699,803 B1 | 6/2020 | Do |
| 10,755,805 B1 | 8/2020 | Do |
| 10,777,302 B2 | 9/2020 | Chowdry |
| 10,790,041 B2 | 9/2020 | Macpherson |
| 10,803,134 B2 | 10/2020 | Kenedy |
| 10,841,312 B2 | 11/2020 | Hawthorne |
| 10,854,318 B2 | 12/2020 | Macpherson |
| 10,891,317 B1 | 1/2021 | Chowdry |
| 10,896,233 B2 | 1/2021 | Kenedy |
| 10,957,455 B2 | 3/2021 | Kenedy |
| 10,991,467 B2 | 4/2021 | Kenedy |
| 10,999,285 B2 | 5/2021 | Hawthorne |
| 11,003,694 B2 | 5/2021 | Kenedy |
| 11,170,047 B2 | 11/2021 | Macpherson |
| 11,170,873 B2 | 11/2021 | Avey |
| 11,171,962 B2 | 11/2021 | Hawthorne |
| 11,667,951 B2 * | 6/2023 | Sawaya ............... C12N 15/10 435/6.11 |
| 2001/0000810 A1 | 5/2001 | Alabaster |
| 2002/0010552 A1 | 1/2002 | Hugh, Jr. |
| 2002/0019746 A1 | 2/2002 | Hugh, Jr. |
| 2002/0048763 A1 | 4/2002 | Penn |
| 2002/0049772 A1 | 4/2002 | Hugh, Jr. |
| 2002/0052697 A1 | 5/2002 | Serita |
| 2002/0052761 A1 | 5/2002 | Fey |
| 2002/0077775 A1 | 6/2002 | Schork |
| 2002/0082868 A1 | 6/2002 | Pories |
| 2002/0094532 A1 | 7/2002 | Bader |
| 2002/0095585 A1 | 7/2002 | Scott |
| 2002/0099789 A1 | 7/2002 | Rudolph |
| 2002/0120623 A1 | 8/2002 | Vivier |
| 2002/0123058 A1 | 9/2002 | Threadgill |
| 2002/0126545 A1 | 9/2002 | Warren |
| 2002/0128860 A1 | 9/2002 | Leveque |
| 2002/0133299 A1 | 9/2002 | Jacob |
| 2002/0133495 A1 | 9/2002 | Hugh, Jr. |
| 2002/0137086 A1 | 9/2002 | Olek |
| 2002/0138572 A1 | 9/2002 | Delany |
| 2002/0155422 A1 | 10/2002 | Ingber |
| 2002/0156043 A1 | 10/2002 | Pfost |
| 2002/0161664 A1 | 10/2002 | Shaya |
| 2002/0169793 A1 | 11/2002 | Sweeney |
| 2002/0174096 A1 | 11/2002 | O'Reilly |
| 2002/0179097 A1 | 12/2002 | Atkins |
| 2002/0183965 A1 | 12/2002 | Gogolak |
| 2002/0187496 A1 | 12/2002 | Andersson |
| 2003/0009295 A1 | 1/2003 | Markowitz |
| 2003/0030637 A1 | 2/2003 | Grinstein |
| 2003/0040002 A1 | 2/2003 | Ledley |
| 2003/0046110 A1 | 3/2003 | Gogolak |
| 2003/0046114 A1 | 3/2003 | Davies |
| 2003/0065241 A1 | 4/2003 | Hohnloser |
| 2003/0065535 A1 | 4/2003 | Karlov |
| 2003/0101000 A1 | 5/2003 | Bader |
| 2003/0113727 A1 | 6/2003 | Girn |
| 2003/0129630 A1 | 7/2003 | Aakalu |
| 2003/0130798 A1 | 7/2003 | Hood |
| 2003/0130873 A1 | 7/2003 | Nevin |
| 2003/0135096 A1 | 7/2003 | Dodds |
| 2003/0135488 A1 | 7/2003 | Amir |
| 2003/0165926 A1 | 9/2003 | Olek |
| 2003/0167260 A1 | 9/2003 | Nakamura |
| 2003/0171876 A1 | 9/2003 | Markowitz |
| 2003/0172065 A1 | 9/2003 | Sorenson |
| 2003/0195706 A1 | 10/2003 | Korenberg |
| 2003/0198970 A1 | 10/2003 | Roberts |
| 2003/0203370 A1 | 10/2003 | Yakhini |
| 2003/0204418 A1 | 10/2003 | Ledley |
| 2003/0208454 A1 | 11/2003 | Hugh, Jr. |
| 2003/0212579 A1 | 11/2003 | Brown |
| 2003/0224394 A1 | 12/2003 | Schadt |
| 2003/0233377 A1 | 12/2003 | Kovac |
| 2003/0237103 A1 | 12/2003 | Jacob |
| 2004/0002816 A1 | 1/2004 | Milosavljevic |
| 2004/0006488 A1 | 1/2004 | Fitall |
| 2004/0009495 A1 | 1/2004 | O'Malley |
| 2004/0014097 A1 | 1/2004 | Mcglennen |
| 2004/0015337 A1 | 1/2004 | Thomas |
| 2004/0018500 A1 | 1/2004 | Glassbrook |
| 2004/0019598 A1 | 1/2004 | Huang |
| 2004/0019688 A1 | 1/2004 | Nickerson |
| 2004/0024534 A1 | 2/2004 | Hsu |
| 2004/0034652 A1 | 2/2004 | Hofmann |
| 2004/0076984 A1 | 4/2004 | Eils |
| 2004/0093331 A1 | 5/2004 | Garner |
| 2004/0093334 A1 | 5/2004 | Scherer |
| 2004/0111410 A1 | 6/2004 | Burgoon |
| 2004/0122705 A1 | 6/2004 | Sabol |
| 2004/0133358 A1 | 7/2004 | Bryant |
| 2004/0146870 A1 | 7/2004 | Liao |
| 2004/0158581 A1 | 8/2004 | Kotlyar |
| 2004/0172287 A1 | 9/2004 | O'Toole |
| 2004/0172313 A1 | 9/2004 | Stein |
| 2004/0175700 A1 | 9/2004 | Geesaman |
| 2004/0177071 A1 | 9/2004 | Massey |
| 2004/0193019 A1 | 9/2004 | Wei |
| 2004/0197799 A1 | 10/2004 | Williamson |
| 2004/0210548 A1 | 10/2004 | William, Jr. |
| 2004/0219493 A1 | 11/2004 | Phillips |
| 2004/0221855 A1 | 11/2004 | Ashton |
| 2004/0235922 A1 | 11/2004 | Baile |
| 2004/0242454 A1 | 12/2004 | Gallant |
| 2004/0243443 A1 | 12/2004 | Asano |
| 2004/0243545 A1 | 12/2004 | Boone |
| 2004/0254920 A1 | 12/2004 | Brill |
| 2005/0003410 A1 | 1/2005 | Frazer |
| 2005/0021240 A1 | 1/2005 | Berlin |
| 2005/0026117 A1 | 2/2005 | Judson |
| 2005/0026119 A1 | 2/2005 | Ellis |
| 2005/0027560 A1 | 2/2005 | Cook |
| 2005/0032066 A1 | 2/2005 | Heng |
| 2005/0037405 A1 | 2/2005 | Caspi |
| 2005/0055365 A1 | 3/2005 | Ramakrishnan |
| 2005/0064476 A1 | 3/2005 | Huang |
| 2005/0090718 A1 | 4/2005 | Dodds |
| 2005/0112684 A1 | 5/2005 | Holzle |
| 2005/0120019 A1 | 6/2005 | Rigoutsos |
| 2005/0143928 A1 | 6/2005 | Moser |

(56) References Cited

U.S. PATENT DOCUMENTS

| | | |
|---|---|---|
| 2005/0152905 A1 | 7/2005 | Omoigui |
| 2005/0154627 A1 | 7/2005 | Zuzek |
| 2005/0158788 A1 | 7/2005 | Schork |
| 2005/0164704 A1 | 7/2005 | Winsor |
| 2005/0170321 A1 | 8/2005 | Scully |
| 2005/0170528 A1 | 8/2005 | West |
| 2005/0176057 A1 | 8/2005 | Bremer |
| 2005/0181516 A1 | 8/2005 | Dressman |
| 2005/0191678 A1 | 9/2005 | Lapointe |
| 2005/0191716 A1 | 9/2005 | Surwit |
| 2005/0191731 A1 | 9/2005 | Judson |
| 2005/0203900 A1 | 9/2005 | Nakamura |
| 2005/0208454 A1 | 9/2005 | Hall |
| 2005/0216208 A1 | 9/2005 | Saito |
| 2005/0228595 A1 | 10/2005 | Cooke |
| 2005/0256649 A1 | 11/2005 | Roses |
| 2005/0260610 A1 | 11/2005 | Kurtz |
| 2005/0278125 A1 | 12/2005 | Harwood |
| 2005/0283386 A1 | 12/2005 | Powers |
| 2006/0020398 A1 | 1/2006 | Vernon |
| 2006/0020614 A1 | 1/2006 | Kolawa |
| 2006/0025929 A1 | 2/2006 | Eglington |
| 2006/0052945 A1 | 3/2006 | Rabinowitz |
| 2006/0059159 A1 | 3/2006 | Truong |
| 2006/0063156 A1 | 3/2006 | Willman |
| 2006/0064415 A1 | 3/2006 | Guyon |
| 2006/0111849 A1 | 5/2006 | Schadt |
| 2006/0129034 A1 | 6/2006 | Kasabov |
| 2006/0129435 A1 | 6/2006 | Smitherman |
| 2006/0136143 A1 | 6/2006 | Avinash |
| 2006/0185027 A1 | 8/2006 | Bartel |
| 2006/0195335 A1 | 8/2006 | Christian |
| 2006/0200319 A1 | 9/2006 | Brown |
| 2006/0218111 A1 | 9/2006 | Cohen |
| 2006/0235881 A1 | 10/2006 | Masarie |
| 2006/0257888 A1 | 11/2006 | Zabeau |
| 2006/0257903 A1 | 11/2006 | Akil |
| 2006/0287876 A1 | 12/2006 | Jedlicka |
| 2006/0293921 A1 | 12/2006 | McCarthy |
| 2007/0011173 A1 | 1/2007 | Agostino |
| 2007/0016568 A1 | 1/2007 | Amir |
| 2007/0027636 A1 | 2/2007 | Rabinowitz |
| 2007/0027850 A1 | 2/2007 | Chan |
| 2007/0027917 A1 | 2/2007 | Ariel |
| 2007/0037182 A1 | 2/2007 | Gaskin |
| 2007/0042369 A1 | 2/2007 | Reese |
| 2007/0050354 A1 | 3/2007 | Rosenberg |
| 2007/0061085 A1 | 3/2007 | Fernandez |
| 2007/0061166 A1 | 3/2007 | Ramasubramanian |
| 2007/0061197 A1 | 3/2007 | Ramer |
| 2007/0061424 A1 | 3/2007 | Mattaway |
| 2007/0078680 A1 | 4/2007 | Wennberg |
| 2007/0082353 A1 | 4/2007 | Hiraoka |
| 2007/0106536 A1 | 5/2007 | Moore |
| 2007/0106754 A1 | 5/2007 | Moore |
| 2007/0111247 A1 | 5/2007 | Stephens |
| 2007/0116036 A1 | 5/2007 | Moore |
| 2007/0122824 A1 | 5/2007 | Tucker |
| 2007/0166728 A1 | 7/2007 | Abramson |
| 2007/0185658 A1 | 8/2007 | Paris |
| 2007/0198485 A1 | 8/2007 | Ramer |
| 2007/0213939 A1 | 9/2007 | Liew |
| 2007/0220017 A1 | 9/2007 | Zuzarte |
| 2007/0226250 A1 | 9/2007 | Mueller |
| 2007/0239554 A1 | 10/2007 | Lin |
| 2007/0244701 A1 | 10/2007 | Erlanger |
| 2007/0254295 A1 | 11/2007 | Harvey |
| 2007/0271292 A1 | 11/2007 | Acharya |
| 2007/0294113 A1 | 12/2007 | Settimi |
| 2007/0299881 A1 | 12/2007 | Bouganim |
| 2008/0009268 A1 | 1/2008 | Ramer |
| 2008/0021288 A1 | 1/2008 | Bowman |
| 2008/0040046 A1 | 2/2008 | Chakraborty |
| 2008/0040151 A1 | 2/2008 | Moore |
| 2008/0081331 A1 | 4/2008 | Myres |
| 2008/0082955 A1 | 4/2008 | Andreessen |
| 2008/0091471 A1 | 4/2008 | Michon |
| 2008/0097938 A1 | 4/2008 | Guyon |
| 2008/0097939 A1 | 4/2008 | Guyon |
| 2008/0108881 A1 | 5/2008 | Stupp |
| 2008/0114617 A1 | 5/2008 | Heniford |
| 2008/0114737 A1 | 5/2008 | Neely |
| 2008/0131887 A1 | 6/2008 | Stephan |
| 2008/0154566 A1 | 6/2008 | Myres |
| 2008/0162510 A1 | 7/2008 | Baio |
| 2008/0189047 A1 | 8/2008 | Wong |
| 2008/0195594 A1 | 8/2008 | Gerjets |
| 2008/0201174 A1 | 8/2008 | Ramasubramanian |
| 2008/0227063 A1 | 9/2008 | Kenedy |
| 2008/0228043 A1 | 9/2008 | Kenedy |
| 2008/0228410 A1 | 9/2008 | Kenedy |
| 2008/0228451 A1 | 9/2008 | Kenedy |
| 2008/0228677 A1 | 9/2008 | Kenedy |
| 2008/0228698 A1 | 9/2008 | Kenedy |
| 2008/0228699 A1 | 9/2008 | Kenedy |
| 2008/0228700 A1 | 9/2008 | Kenedy |
| 2008/0228701 A1 | 9/2008 | Kenedy |
| 2008/0228702 A1 | 9/2008 | Kenedy |
| 2008/0228704 A1 | 9/2008 | Kenedy |
| 2008/0228705 A1 | 9/2008 | Kenedy |
| 2008/0228706 A1 | 9/2008 | Kenedy |
| 2008/0228708 A1 | 9/2008 | Kenedy |
| 2008/0228722 A1 | 9/2008 | Kenedy |
| 2008/0228753 A1 | 9/2008 | Kenedy |
| 2008/0228756 A1 | 9/2008 | Kenedy |
| 2008/0228757 A1 | 9/2008 | Kenedy |
| 2008/0228765 A1 | 9/2008 | Kenedy |
| 2008/0228766 A1 | 9/2008 | Kenedy |
| 2008/0228767 A1 | 9/2008 | Kenedy |
| 2008/0228768 A1 | 9/2008 | Kenedy |
| 2008/0228797 A1 | 9/2008 | Kenedy |
| 2008/0243843 A1 | 10/2008 | Kenedy |
| 2008/0256023 A1 | 10/2008 | Nair |
| 2008/0286761 A1 | 11/2008 | Day |
| 2008/0286796 A1 | 11/2008 | Grupe |
| 2008/0300958 A1 | 12/2008 | Gluck |
| 2009/0012928 A1 | 1/2009 | Lussier |
| 2009/0029371 A1 | 1/2009 | Elliott |
| 2009/0043752 A1 | 2/2009 | Kenedy |
| 2009/0077110 A1 | 3/2009 | Petri |
| 2009/0083654 A1 | 3/2009 | Nickerson |
| 2009/0099789 A1 | 4/2009 | Stephan |
| 2009/0112871 A1 | 4/2009 | Hawthorne |
| 2009/0118131 A1 | 5/2009 | Avey |
| 2009/0119083 A1 | 5/2009 | Avey |
| 2009/0132284 A1 | 5/2009 | Fey |
| 2009/0186347 A1 | 7/2009 | Cox |
| 2009/0222517 A1 | 9/2009 | Kalofonos |
| 2009/0271375 A1 | 10/2009 | Hyde |
| 2009/0299645 A1 | 12/2009 | Colby |
| 2009/0318297 A1 | 12/2009 | Cappucilli |
| 2009/0319610 A1 | 12/2009 | Nikolayev |
| 2009/0326832 A1 | 12/2009 | Heckerman |
| 2010/0024894 A1 | 2/2010 | Himmelmann |
| 2010/0041958 A1 | 2/2010 | Leuthardt |
| 2010/0042438 A1 | 2/2010 | Moore |
| 2010/0042643 A1 | 2/2010 | Pattabhi |
| 2010/0063830 A1 | 3/2010 | Kenedy |
| 2010/0063835 A1 | 3/2010 | Kenedy |
| 2010/0063865 A1 | 3/2010 | Kenedy |
| 2010/0063930 A1 | 3/2010 | Kenedy |
| 2010/0070292 A1 | 3/2010 | Kenedy |
| 2010/0070455 A1 | 3/2010 | Halperin |
| 2010/0076950 A1 | 3/2010 | Kenedy |
| 2010/0076988 A1 | 3/2010 | Kenedy |
| 2010/0099091 A1 | 4/2010 | Hamet |
| 2010/0169262 A1 | 7/2010 | Kenedy |
| 2010/0169313 A1 | 7/2010 | Kenedy |
| 2010/0169338 A1 | 7/2010 | Kenedy |
| 2010/0223281 A1 | 9/2010 | Hon |
| 2011/0004628 A1 | 1/2011 | Armstrong |
| 2011/0078168 A1 | 3/2011 | Kenedy |
| 2011/0098187 A1 | 4/2011 | Urdea |
| 2011/0098193 A1 | 4/2011 | Kingsmore |

(56) References Cited

U.S. PATENT DOCUMENTS

| | | |
|---|---|---|
| 2011/0184656 A1 | 7/2011 | Kenedy |
| 2011/0196872 A1 | 8/2011 | Sims |
| 2012/0035954 A1 | 2/2012 | Yeskel |
| 2012/0053845 A1 | 3/2012 | Bruestle |
| 2012/0270190 A1 | 10/2012 | Kenedy |
| 2012/0270794 A1 | 10/2012 | Eriksson |
| 2012/0309639 A1 | 12/2012 | Hakonarson |
| 2013/0013217 A1 | 1/2013 | Stephan |
| 2013/0085728 A1 | 4/2013 | Tang |
| 2013/0129630 A1 | 5/2013 | Haik |
| 2013/0345988 A1 | 12/2013 | Avey |
| 2014/0067355 A1 | 3/2014 | Noto |
| 2014/0098344 A1 | 4/2014 | Gierhart |
| 2015/0051086 A1 | 2/2015 | Hatchwell |
| 2015/0248473 A1 | 9/2015 | Kenedy |
| 2015/0288780 A1 | 10/2015 | El Daher |
| 2015/0315645 A1 | 11/2015 | Gaasterland |
| 2015/0347566 A1 | 12/2015 | Kenedy |
| 2015/0356243 A1 | 12/2015 | Andreassen |
| 2016/0026755 A1 | 1/2016 | Byrnes |
| 2016/0042143 A1 | 2/2016 | Kenedy |
| 2016/0091499 A1 | 3/2016 | Sterling |
| 2016/0103950 A1 | 4/2016 | Myres |
| 2016/0171155 A1 | 6/2016 | Do |
| 2016/0277408 A1 | 9/2016 | Hawthorne |
| 2017/0053089 A1 | 2/2017 | Kenedy |
| 2017/0185719 A1 | 6/2017 | Kenedy |
| 2017/0277828 A1 | 9/2017 | Avey |
| 2017/0330358 A1 | 11/2017 | Macpherson |
| 2018/0181710 A1 | 6/2018 | Avey |
| 2018/0210705 A1 | 7/2018 | Kenedy |
| 2018/0239831 A1 | 8/2018 | Boyce |
| 2019/0034163 A1 | 1/2019 | Kenedy |
| 2019/0206514 A1 | 7/2019 | Avey |
| 2019/0267115 A1 | 8/2019 | Avey |
| 2019/0281061 A1 | 9/2019 | Hawthorne |
| 2020/0137063 A1 | 4/2020 | Hawthorne |
| 2020/0210143 A1 | 7/2020 | Kenedy |
| 2021/0058398 A1 | 2/2021 | Hawthorne |
| 2021/0166823 A1 | 6/2021 | Kenedy |
| 2021/0209134 A1 | 7/2021 | Kenedy |
| 2021/0233665 A1 | 7/2021 | Kenedy |
| 2021/0250357 A1 | 8/2021 | Hawthorne |

FOREIGN PATENT DOCUMENTS

| | | |
|---|---|---|
| WO | 1992010092 A1 | 6/1992 |
| WO | 200127857 W | 4/2001 |
| WO | 200150214 W | 7/2001 |
| WO | 200210456 W | 2/2002 |
| WO | 200222165 W | 3/2002 |
| WO | 2002080079 A2 | 10/2002 |
| WO | 2003060652 A2 | 7/2003 |
| WO | 2003076895 A2 | 9/2003 |
| WO | 2004029298 A2 | 4/2004 |
| WO | 2004031912 A2 | 4/2004 |
| WO | 2004048551 A2 | 6/2004 |
| WO | 2004051548 A2 | 6/2004 |
| WO | 2004075010 A2 | 9/2004 |
| WO | 2004097577 A2 | 11/2004 |
| WO | 2005086891 A2 | 9/2005 |
| WO | 2005109238 A2 | 11/2005 |
| WO | 2006052952 A2 | 5/2006 |
| WO | 2006084195 A2 | 8/2006 |
| WO | 2006089238 A2 | 8/2006 |
| WO | 2007061881 A2 | 5/2007 |
| WO | 2008042232 A2 | 4/2008 |
| WO | 2008067551 A2 | 6/2008 |
| WO | 2009051749 A1 | 4/2009 |
| WO | 2009051766 A1 | 4/2009 |
| WO | 2009051768 A1 | 4/2009 |
| WO | 2010065139 A1 | 6/2010 |
| WO | 2010139006 A1 | 12/2010 |

OTHER PUBLICATIONS

Notice of Allowance, U.S. Appl. No. 17/077,930, dated May 4, 2022.
Notice of Allowance, U.S. Appl. No. 17/175,995, dated Nov. 14, 2022.
Notice of Allowance, U.S. Appl. No. 17/212,596, dated Oct. 11, 2022.
Notice of Allowance, U.S. Appl. No. 17/212,906, dated Oct. 19, 2022.
Notice of Allowance, U.S. Appl. No. 17/351,052, dated Mar. 4, 2022.
Notice of Allowance, U.S. Appl. No. 17/576,738, dated Jul. 26, 2022.
Notice of Allowance, U.S. Appl. No. 17/584,844, dated Apr. 21, 2022.
Notice of Allowance, U.S. Appl. No. 17/590,304, dated Apr. 25, 2022.
Notice of Allowance, U.S. Appl. No. 17/729,840, dated Oct. 11, 2022.
Notice of Allowance, U.S. Appl. No. 17/731,779, dated Oct. 3, 2022.
Notice of Allowance, U.S. Appl. No. 17/731,963, dated Oct. 18, 2022.
Notice of Allowance, U.S. Appl. No. 17/743,973 dated Oct. 25, 2022.
Notice of Allowance, U.S. Appl. No. 17/873,563, dated Sep. 14, 2022.
Nuanmeesri, et al., "Genealogical Information Searching System" 2008 4th IEEE International Conference on Management of Innovation and Technology. IEEE, 2008, pp. 1255-1259.
Nyholt et al., "Genetic basis of male pattern baldness" J. Invest. Dermatol. 121 (2003) pp. 1561-1564.
Nyholt, Dale R., "Genehunter: Your 'One-Stop Shop' for Statistical Genetic Analysis?" Hum. Hered. 53 (2002) pp. 2-7.
O'Connell, J.R., "Rapid multipoint linkage analysis via inheritance vectors in the Elston-Stewart algorithm" Hum. Hered. 51, (2001) pp. 226-240.
O'Connell, J.R., "The VITESSE algorithm for rapid exact multilocus linkage analysis via genotype set-recoding and fuzzy inheritance" Nature. Genet. 11, (1995) pp. 402-408.
Office Action, U.S. Appl. No. 12/644,791, dated May 31, 2012.
Office Action, U.S. Appl. No. 12/644,791, dated Dec. 7, 2012.
Office Action, U.S. Appl. No. 12/774,546, dated Aug. 12, 2015.
Office Action, U.S. Appl. No. 12/774,546, dated Feb. 2, 2016.
Office Action, U.S. Appl. No. 12/774,546, dated Feb. 1, 2017.
Office Action, U.S. Appl. No. 13/871,744, dated Feb. 18, 2016.
Office Action, U.S. Appl. No. 14/822,023, dated Feb. 21, 2017.
Office Action, U.S. Appl. No. 14/822,023, dated Nov. 22, 2017.
Office Action, U.S. Appl. No. 15/264,493, dated May 18, 2018.
Office Action, U.S. Appl. No. 15/443,739, dated Dec. 10, 2019.
Office Action, U.S. Appl. No. 15/664,619, dated Mar. 3, 2020.
Office Action, U.S. Appl. No. 15/927,785, dated Feb. 10, 2020.
Office Action, U.S. Appl. No. 15/999,198, dated Aug. 5, 2020.
Office Action, U.S. Appl. No. 16/129,645, dated Apr. 23, 2021.
Office Action, U.S. Appl. No. 16/151,721, dated Jan. 25, 2021.
Office Action, U.S. Appl. No. 16/151,721, dated Oct. 26, 2021.
Office Action, U.S. Appl. No. 16/814,243, dated Jul. 1, 2020.
Office Action, U.S. Appl. No. 16/814,243, dated Nov. 16, 2020.
Office Action, U.S. Appl. No. 16/814,243, dated Dec. 9, 2021.
Office Action, U.S. Appl. No. 16/814,243, dated Jun. 22, 2022.
Office Action, U.S. Appl. No. 17/004,494, dated Nov. 6, 2020.
Office Action, U.S. Appl. No. 17/004,911, dated Nov. 18, 2020.
Office Action, U.S. Appl. No. 17/073,122, dated Dec. 24, 2020.
Office Action, U.S. Appl. No. 17/073,122, dated Jun. 14, 2021.
Office Action, U.S. Appl. No. 17/073,128, dated Feb. 3, 2021.
Office Action, U.S. Appl. No. 17/073,128, dated Jun. 30, 2021.
Office Action, U.S. Appl. No. 17/077,930, dated Dec. 21, 2020.
Office Action, U.S. Appl. No. 17/077,930, dated Apr. 20, 2021.
Office Action, U.S. Appl. No. 17/077,930, dated Nov. 16, 2021.
Office Action, U.S. Appl. No. 17/175,995, dated Oct. 19, 2022.
Office Action, U.S. Appl. No. 17/212,596, dated Sep. 19, 2022.

(56) References Cited

OTHER PUBLICATIONS

Chiasson, JL et al., "Acarbose for prevention of type 2 diabetes mellitus: the STOP-NIDDM randomised trial", Lancet 359, (2002) pp. 2072-2077.
Choi, et al., "Case-control association testing in the presence of unknown relationships" Genet. Epidem. 33, (2009) pp. 668-678.
Cockerman, C., "Higher order probability functions of identity of alleles by descent" Genetics 69, (1971) pp. 235-246.
Complaint filed in the United States District Court in and for the Northern District of California, captioned *23andMe, Inc. v. Ancestry.com DNA, LLC, Ancestry.com Operations Inc.*, and *Ancestry.com LLC*, filed on May 11, 2018, assigned Case No. 18-cv-02791-JCS, for "Complaint for Patent Infringement, Violations of the Lanham Act, Cal. Bus. & Prof. Code§§ 17200 and 17500, and Declaratory Relief of No Trademark Infringement and Trademark Invalidity."
Cooper, D. N. & Krawczak, M. The mutational spectrum of single base-pair substitutions causing human genetic disease: patterns and predictions. Human Genetics 85, 55-74 (1990).
Cordell, et al., "Two-locus maximum Lod score analysis of a multifactorial trait: joint consideration of IDDM2 and IDDM4 with IDDM1 in Type 1 diabetes" Am. J. Hum. Genet. 57, (1995) pp. 920-934.
Cowell, R.G., "FINEX: A probabilistic expert system for forensic identification" Forensic Science International, 134, (2003) pp. 196-206.
Crawford, et al., "Evidence for substantial fine-scale variation in recombination rates across the human genome," Nature Genetics, vol. 36, No. 7, Jul. 2004, pp. 700-706.
Cudworth, et al., "Evidence for HL-A-linked genes in "juvenile" diabetes mellitus" Br. Med. J. 3, (1975) pp. 133-135.
Curtis, et al., "Using risk calculation to implement an extended relative pair analysis" Ann. Hum. Genet. 58 (1994) pp. 151-162.
Das, S., "Filters, Wrappers and a Boosting-Based Hybrid for Feature Selection", In Proceedings of the Eighteenth International Conference on Machine Learning, Jun. 28, 2001, pp. 74-81.
Davis et al., "The overall pattern of cardiac contraction depends on a spatial gradient of myosin regulatory light chain phosphorylation", Cell 107 (2001) pp. 631-641.
Dawid, P., "Present Position and Potential Developments: Some Personal Views: Statistical Theory: The Prequential Approach", Journal of the Royal Statistical Society, Series A {General), vol. 147, No. 2, (1984) pp. 278-292.
Defendants' Notice of Motion and Motion to Dismiss Plaintiff's Complaint, filed in the United States District Court in and for the Northern District of California LLC on Jun. 29, 2018, Case No. 18-cv-02791-JCS, Re *23andMe, Inc. v. Ancestry.com DNA, LLC, Ancestry.com Operations Inc.*, and *Ancestry.com*.
Denniston, C., "Probability and genetic relationship" Ann. Hum. Genet., Lond. (1975), 39, pp. 89-103.
Devlin and Roeder, "Genomic control for association studies" Biometrics 55(4) (1999) pp. 997-1004.
Di Fonzo A. et al., "ATP13A2 missense mutations in juvenile parkinsonism and young onset Parkinson disease" Neurology 68 (2007) pp. 1557-1562.
Di Rienzo, et al., "An evolutionary framework for common diseases: the ancestral-susceptibility model" Trends Genet. 21 (2005) pp. 596-601.
Dodds, Ken G., Peter R Amer, and Benoit Auvray, "Using genetic markers in unpedigreed populations to detect a heritable trait", Journal of Zhejiang University Science B 8, No. 11 (2007): 782-786.
Donnelly, K.P., "The probability that related individuals share some section of genome identical by descent" Theor. Popul. Biol. 23 (1983) pp. 34-63.
Douglas, et al., "A multipoint method for detecting genotyping errors and mutations in sibling pair linkage data" Am. J. Hum. Genet. 66 (2000) pp. 1287-1297.
Duan, K.-B. B., Rajapakse, J. C., Wang, H. & Azuaje, F. Multiple svm-rfe for gene selection in cancer classification with expression data. IEEE transactions on nanobioscience 4, 228-234 (2005).

Duffy, et al. "An integrated genetic map for linkage analysis" Behav. Genet. 36, 2006, pp. 4-6.
Dupuis, et al., "Statistical methods for linkage analysis of complex traits from high resolution maps of identity by descent" Genetics 140 (1995) pp. 843-856.
Eding, et al., "Marker-based estimates of between and within population kinships for the conservation of genetic diversity" J. Anim. Breed. Genet. 118 (2001 ), pp. 141-159.
Edmonds J. and Karp R., "Theoretical improvements in algorithmic efficiency for network flow problems" J ACM 19, (1972) pp. 248-264.
Ehm, et al., "A test statistic to detect errors in sib-pair relationships" Am. J. Hum. Genet. 62 (1998) pp. 181-188.
Ellis et al., "Polymorphism of the androgen receptor gene is associated with male pattern baldness" Dermatol. 116 (2001) pp. 452-455.
Elston, et al., "A general model for the genetic analysis of pedigree data" Hum. Hered. 21, (1971) pp. 523-542.
Epstein, et al., "Improved inference of relationship for pairs of individuals" Am. J. Hum. Genet., vol. 67, (2000) pp. 1219-1231.
European Patent Office, Extended European Search Report, App. No. 09836517.4, dated Oct. 25, 2016.
European Patent Office, Extended European Search Report, App. No. 17172048.5, dated Oct. 9, 2017.
European Patent Office, Office Action, App. No. 17172048.5, dated Oct. 27, 2021.
Expert Panel, "Obesity in Adults" NIH Publication No. 98-4083, Sep. 1998, National Institute of Health, pp. 1-228.
Falconer et al., "Endometriosis and genetic polymorphisms" Obstet Gynecol Surv 62(9) (2007) pp. 616-628.
Falush, et al., "Inference of population structure using multilocus genotype data:linked loci and correlated allele frequencies" Genetics 164, (2003) pp. 1567-1587.
Farrer M.J., "Genetics of Parkinson disease: paradigm shifts and future prospects" Nat Rev Genet 7, (2006) pp. 306-318.
Feingold, E. "Markov processes for modeling and analyzing a new genetic mapping method" J. Appl. Prob. 30 (1993) pp. 766-779.
Feingold, et al., "Gaussian Models for Genetic Linkage Analysis Using Complete High-Resolution Maps of Identity by Descent," Am. J. Hum. Genet. 53 (1993) pp. 234-251.
Fisher, RA "A Fuller Theory of 'Junctions' in Inbreeding" Heredity, 8 (1954) pp. 187-197.
Fisher, RA "The theory of inbreeding" Department of Genetics, Cambridge University, Eng. Edinburgh, London, Oliver & Boyd, Ltd., (1949) pp. 97-100.
Frazer, et al., "A second generation human haplotype map of over 3 .1 million SNPs", vol. 449, Oct. 18, 2007, pp. 851-861. <doi:I0.1038/nature06258>.
Freidlin B. et al., "Trend tests for case-control studies of genetic markers: power, sample size and robustness" Hum Hered 53(2002) pp. 146-152.
Gail, M.H. et al., "Projecting individualized probabilities of developing breast cancer for white females who are being examined annually" J. Natl. Cancer Inst., vol. 81, No. 24, Dec. 20, 1989, pp. 1879-1886.
Garrett, Paul: The mathematics of coding: Information, compression, error correction and finite fields. University of Minnesota. Downloaded Apr. 13, 2021 (Year: 2021).
Gaytmenn, et al., "Determination of the sensitivity and specificity of sibhip calculations using AmpF/STR Profiler Plus" Int. J. Legal Med. 116, (2002) pp. 161-164.
George, et al., "Discovering disease genes: Multipoint linkage analyses via a new Markov Chain Monte Carlo approach" Statistical Science, vol. 18, No. 4, (2003) pp. 515-535.
Gillanders, et al., "The Value of Molecular Haplotypes in a Family-Based Linkage Study" Am. J. Hum. Genet. 79 (2006) pp. 458-468.
Glaubitz, Jeffrey C., O. Eugene Rhodes Jr, and J. Andrew Dewoody_ "Prospects for inferring pairwise relationships with single nucleotide polymorphisms", Molecular Ecology 12, No. 4 (2003): 1039-1047.
Office Action, U.S. Appl. No. 17/212,906, dated May 12, 2022.
Office Action, U.S. Appl. No. 17/212,906, dated Jun. 24, 2022.
Office Action, U.S. Appl. No. 17/301,129, dated Jun. 8, 2021.

(56) References Cited

OTHER PUBLICATIONS

Office Action, U.S. Appl. No. 17/351,052, dated Dec. 9, 2021.
Office Action, U.S. Appl. No. 17/576,738, dated Apr. 14, 2022.
Office Action, U.S. Appl. No. 17/584,844, dated Mar. 28, 2022.
Office Action, U.S. Appl. No. 17/590,304, dated Apr. 4, 2022.
Office Action, U.S. Appl. No. 17/729,840, dated Jun. 22, 2022.
Office Action, U.S. Appl. No. 17/731,779, dated Jun. 16, 2022.
Office Action, U.S. Appl. No. 17/731,963, dated Jun. 28, 2022.
Office Action, U.S. Appl. No. 17/743,973, dated Jul. 14, 2022.
Oliehoek, et al., "Estimating relatedness between individuals in general populations with a focus on their use in conservation programs" Genetics 173 (2006) pp. 483-496.
Olson, et al., "Relationship estimation by Markov-process models in sib-pair linkage study" Am. J. Hum. Genet. 64, (1999) pp. 1464-1472.
Opposition to Defendants' Motion to Dismiss Plaintiff's Complaint, filed in the United States District Court in and for the Northern District of California LLC on Jul. 13, 2018, Case No. 18-cv-02791-JCS, Re *23andMe, Inc.* v. *Ancestry.com DNA, LLC, Ancestry.com Operations Inc.*, and *Ancestry.com*.
Order Granting in Part and Denying in Part Defendants' Motion to Dismiss, dated Aug. 23, 2018, Case No. 18-cv-02791-JCS, from the United States District Court in and for the Northern District of California LLC, Re *23andMe, Inc.* v. *Ancestry.com DNA, LLC, Ancestry.com Operations Inc.*, and *Ancestry.com*.
Orlin J.B. and Lee Y., "QuickMatch: a very fast algorithm for the assignment problem", MIT Sloan School Working Paper, Mar. 1993, pp. 3547-3593.
Patterson, et al., "Population Structure and Eigenanalysis," PLoS Genetics, vol. 2, No. 12, e190, Dec. 2006, pp. 2074-2093.
Payami H., et al., "Familial aggregation of Parkinson disease: a comparative study of early-onset and late-onset disease", Arch Neurol. 59, (2002) pp. 848-850.
Paynter, et al., "Accuracy of Multiplexed Illumina Platform-Based Single-Nucleotide Polymorphism Genotyping Compared between Genomic and Whole Genome Amplified DNA Collected from Multiple Sources," Cancer Epidemiol Biomarkers Prev. 15, Dec. 2006, pp. 2533-2536.
Peedicayil, J., "Epigenetic Therapy—a New Development in Pharmacology", Indian Journal of Medical Research, vol. 123, No. 1, Jan. 2006, pp. 17-24.
Pemberton et al., "Inference of unexpected Genetic relatedness among individuals in HapMap phase III" Am. J. Hum. Genet. 87, (2010) pp. 457-464.
Perry, et al., "The fine-scale and complex architecture of human copy-number variation," Am. J. Hum. Genet. 82, Mar. 2008, pp. 685-695.
Pierpont et al., "Genetic basis for congenital heart defects: current knowledge: a scientific statement from the American Heart Association Congenital Cardiac Defects Committee, Council on Cardiovascular disease in the Young: endorsed by the American Academy of Pediatrics", Circulation 115(23) (2007), pp. 3015-3038.
Pinto, et al., "Copy-number variation in control population cohorts," Human Molecular Genetics, 2007, vol. 16, review issue No. 2, pp. R168-R173. doi:10.1093/hmg/ddm241.
Polymeropoulos et al., "Mutation in the alpha-synuclein gene identified in families with Parkinson's disease", Science 276 (1997), pp. 2045-2047.
Porras-Hurtado, et al., "An overview of Structure: applications, parameter settings, and supporting software," Frontiers in Genetics, vol. 4, No. 96, May 29, 2013, pp. 1-13.
Prather, et al., "Medical data mining: knowledge discovery in a clinical data warehouse, Fall 1997, Proceedings of the AMIA Annual Fall Symposium, pp. 101-105.
Pritchard et al., "Linkage Disequilibrium in Humans: Models and Data", Am. J. Hum. Genet. 69 (2001), pp. 1-14.
Pritchard, et al., "Association Mapping in Structured Populations," Am. J. Hum. Genet., vol. 67, 2000, pp. 170-181.
Pritchard, et al., "Inference of population structure using multilocus genotype data" Genetics 155, (2000) pp. 945-959.
Purcell, et al., "PLINK: a toolset for whole-genome association and population-based linkage analysis", Am. J. Hum. Genet., vol. 81, Sep. 2007, pp. 559-575.
Queller, et al., "Estimating relatedness using genetic markers" Evolution, vol. 43, No. 2, (1989) pp. 258-275.
Rabiner, L., "A Tutorial on Hidden Markov Models and Selected Applications in Speech Recognition," Proceedings of the IEEE, vol. 77, No. 2, Feb. 1989, pp. 257-286.
Rahman, M. et al, "A simple risk score identifies individuals at high risk of developing type 2 diabetes: a prospective cohort study", Fam. Pract. 2008;25, pp. 191-196.
Ramirez A. et al., "Hereditary parkinsonism with dementia is caused by mutations in ATP13A2, encoding a lysosomal type 5 P-type ATPase", Nat. Genet. 38 (2006) pp. 1184-1191.
Rannala, et al., "Detecting immigration by using multilocus genotypes" Proc. Natl. Acad. Sci. USA 94, (1997) pp. 9197-9201.
Rastas, et al., "A hidden Markov technique for haplotype reconstruction" Leet. Notes Comput. Sci. 3692, (2005) pp. 140-151.
Ratovitski et al., "Kalirin inhibition of inducible nitric—oxide synthase", J. Biol. Chem. 274 (1999) pp. 993-999.
Reczek D. et al., "LIMP-2 Is a Receptor for Lysosomal Mannose-6-Phosphate-Independent Targeting of beta-Glucocerebrosidase", Cell, Nov. 16; 131(4) (2007), pp. 770-783.
Redon, et al., "Global variation in copy number in the human genome," Nature vol. 444, Nov. 23, 2006, pp. 444-454. doi:10.1038/nature05329.
Reid, et al., "Specificity of sibship determination using the ABI identifier multiplex system" J. Forensic Sci. 49, (2004) pp. 1262-1264.
Ren and Fang, "Small guanine nucleotide-binding protein Rho and myocardial function", Acta Pharmacol. Sin. 26(3) (2005), pp. 279-285.
Reply Brief of Appellant 23AndMe, Inc., Case No. 2019-1222, Document: 25, Filed on Apr. 8, 2019, In the US Court of Appeals for Federal Circuit, pp. 1-38.
Riquet, J. et al., "Fine-mapping of quantitative trait loci by identity by descent in outbred populations: application to milk production in dairy cattle," Proceedings of the National Academy of Sciences, vol. 96, No. 16, Aug. 3, 1999, pp. 9252-9257. doi: 10.1073/pnas.96.16.9252.
Risch, et al., "Linkage strategies for genetically complex traits. II. The power of affected relative pairs" Am. J. Hum. Genet. 46 (1990) pp. 229-241.
Ritland, et al., "Inferences about quantitative inheritance based on natural population structure in the yellow monkeyflower, Mimulus Guttatus" Evolution 50, (1996) pp. 1074-1082.
Ritland, K., "A marker-based method for inferences about quantitative inheritance in natural populations" Evolution 50, (1996b) pp. 1062-1073.
Ritland, K., "Estimators for pairwise relatedness and individual inbreeding coefficients" Genet. Res. 67 (1996a) pp. 175-185.
Jones, et al., "Methods of parentage analysis in natural populations" Molecular Ecology 12 (2003) pp. 2511-2523.
Karigl, G., "A recursive algorithm for the calculation of identity coefficients" Ann. Hum. Genet. 45, (1981) pp. 299-305.
Katzmarzyk, et al., "Adiposity, physical fitness and incident diabetes: the physical activity longitudinal study" Diabetologia 50, (2007) pp. 538-544.
Keith, Jonathan M., Allan McRae, David Duffy, Kerrie Mengersen, and Peter M. Visscher. "Calculation of IBD probabilities with dense SNP or sequence data", Genetic Epidemiology: The Official Publication of the International Genetic Epidemiology Society 32, No. 6 (2008): 513-519.
Kent, J.W. "BLAT—The BLAST-Like Alignment Tool" Genome Res. 2002, vol. 12, pp. 656-664.
Keprt, et al., "Binary factor analysis with help of formal concepts" In Snasel et al (eds) CLA 2004, pp. 90-101. ISBN 80-248-0597-9.
Kettel et al., "Treatment of endometriosis with the antiprogesterone mifepristone" Fertil. Steril. 65(1) (1996) pp. 23-28.
Kimmel, et al., "A block-free hidden Markov model for genotypes and its application to disease association" J. Comput. Biol. 12, (2005a) pp. 1243-1260.

(56) References Cited

OTHER PUBLICATIONS

Kimmel, et al., "GERBIL: genotype resolution and block identification using likelihood" Proc. Natl. Acad. Sci. USA 102, (2005b) pp. 158-162.

Kitada T. et al., "Mutations in the parkin gene cause autosomal recessive juvenile parkinsonism" Nature 392 (1998) pp. 605-608.

Klein, T. E. et al. Integrating genotype and phenotype information: an overview of the PharmGKB project. The Pharmacogenomics Journal 1, 167-170 (2001).

Knowler, et al., "Reduction in the incidence of type 2 diabetes with lifestyle intervention or metformin" N. Engl. J. Med. 346, (2002) pp. 393-403.

Kong, Augustine, Gisli Masson, Michael L. Frigge, Arnaldur Gylfason, Pasha Zusmanovich, Gudmar Thorleifsson, Pall I. Olason et al., "Detection of sharing by descent, long-range phasing and haplotype imputation", Nature genetics 40, No. 9 (2008): 1068-1075.

Kong, et al., "A combined linkage-physical map of the human genome," Am. J. Hum. Genet., vol. 75, 2004, pp. 1143-1148.

Kong, et al., "A high-resolution recombination map of the human genome" Nature Genetics, vol. 31, Jul. 2002, pp. 241-247.

Kong, et al., "Allele-sharing models—LOO scores and accurate linkage tests" Am. J. Hum. Genet. 61, (1997) pp. 1179-1188.

Kruger et al. "Ala30Pro mutation in the gene encoding alpha-synuclein in Parkinson's disease" Nature Genetics, vol. 18, Feb. 1998, pp. 106-108.

Kruglyak, et al., "Complete Multipoint Sib-Pair Analysis of Qualitative and Quantitative Traits" Am. J. Hum. Genet. 57, (1995) pp. 439-454.

Kruglyak, et al., "Faster multipoint linkage analysis using Fourier transforms" J. Comput. Biol. 5, (1998) pp. 1-7.

Kruglyak, et al., "Linkage thresholds for two-stage genome scans" Am. J. Hum. Genet. 62, (1998) pp. 994-997.

Kruglyak, et al., "Parametric and Nonparametric Linkage Analysis: A Unified Multipoint Approach" Am. J. Hum. Genet. 58, (1996) pp. 1347-1363.

Kruglyak, et al., "Rapid Multipoint Linkage Analysis of Recessive Traits in Nuclear Families, Including Homozygosity Mapping" Am. J. Hum. Genet. 56 (1995) pp. 519-527.

Kruglyak, L., "The use of a genetic map of biallelic markers in linkage studies" Nat. Genet. 17, (1997) pp. 21-24.

Kumar, et al., "Recurrent 16p11.2 microdeletions in autism" Human Molecular Genetics, 2008, vol. 17, No. 4, pp. 628-638.

Laberge, et al., "Population history and its impact on medical genetics in Quebec" Clin. Genet. 68 (2005) pp. 287-301.

Lafrate, et al., "Detection of large-scale variation in the human genome," Nature Genetics, vol. 36, No. 9, Sep. 2004, pp. 949-951.

Lander, et al., "Construction of multilocus genetic linkage maps in humans" Genetics, vol. 84, Apr. 1987, pp. 2363-2367.

Lander, et al., "Genetic dissection of complex traits: guidelines for interpreting and reporting linkage results" Nat. Genet. 11, (1995) pp. 241-247.

Lander, et al., "Homozygosity mapping: a way to map human recessive traits with the DNA of inbred children" Science 236, (1987) pp. 1567-1570.

Lange, et al., "Extensions to pedigree analysis I. Likelihood calculations for simple and complex pedigrees" Hum. Hered. 25 (1975) pp. 95-105.

Lavenier, Dominique, and J-L. Pacherie. "Parallel processing for scanning genomic databases." Advances in Parallel Computing. vol. 12, North-Holland, 1998, pp. 81-88.

Leclair, et al., "Enhanced kinship analysis and STR-based DNA typing for human identification in mass fatality incidents: The Swissair Flight 111 disaster" Journal of Forensic Sciences, 49(5) (2004) pp. 939-953.

Leibon, et al., "A simple computational method for the identification of disease-associated loci in complex, incomplete pedigrees" arXiv:0710:5625v1 [q-bio.GN] Oct. 30, 2007, pp. 1-20.

Leibon, Gregory, Daniel N. Rockmore, and Martin R Pollak, "A SNP streak model for the identification of genetic regions identical-by-descent", Statistical Applications in Genetics and Molecular Biology 7, No. 1 (2008).

Leutenegger, et al., "Estimation of the Inbreeding Coefficient through Use of Genomic Data," Am. J. Hum. Genet. 73, Jul. 29, 2003, pp. 516-523.

Leutenegger, et al., "Using genomic inbreeding coefficient estimates for homozygosity mapping of rare recessive traits: Application to Taybi-Linder syndrome" Am. J. Hum. Genet., vol. 79, Jul. 2006, pp. 62-66.

Li Y. et al., "Genetic evidence for ubiquitin-specific proteases USP24 and USP40 as candidate genes for late-onset Parkinson disease" Hum Mutat 27(10) (2006) pp. 1017-1023.

Li, et al., "Fast and accurate long-read alignment with Burrows-Wheeler transform" Bioinformatics vol. 26, No. 5, 2010, pp. 589-595.

Li, et al., "Joint modeling of linkage and association: identifying SNPs responsible for a linkage signal" Am. J. Hum. Genet. 76 (2005) pp. 934-949.

Li, et al., "Mapping short DNA sequencing reads and calling variants using mapping quality scores," Genome Research, Aug. 19, 2008, pp. 1851-1858. doi:10.1101/gr.078212.108.

Li, et al., "Modeling linkage disequilibrium and identifying recombination hotspots using single nucleotide polymorphism data" Genetics 165, (2003) pp. 2213-2233.

Li, et al., "Similarity of DNA fingerprints due to chance and relatedness" Hum. Hered. 43, 1993 pp. 45-52.

Lien, et al. "Evidence for heterogeneity in recombination in the human pseudoautosomal region: High resolution analysis by sperm typing and radiation-hybrid mapping" Am. J. Hum. Genet. 66, 2000, pp. 557-566.

Lin, et al. "Haplotype inference in random population samples" Am. J. Hum. Genet. 71, 2002, pp. 1129-1137.

Lindstrom, J. et al., "The diabetes risk score: a practical tool to predict type 2 diabetes risk" Diabetes Care 26:3 (2003) pp. 725-731.

Liu, et al., "Affected sib-pair test in inbred populations" Ann. Hum. Genet. 68, (2004) pp. 606-619.

Lo et al., "Epidemiology and adverse cardiovascular risk profile of diagnosed polycystic ovary syndrome" J. Clin. Endocrinol. Metab. 91 (2006) pp. 1357-1363.

Lobo, et al., "AUC: a misleading measure of the performance of predictive distribution models" Global Ecology and Biogeography, (2007) pp. 1-7. <doi:10.1111/j.1466-8238.2007.00358.x>.

Long, et al., "An E-M Algorithm and Testing Strategy for Multiple-Locus Haplotypes" Am. J. Hum. Genet. 56 (1995) pp. 799-810.

Cartier, Kevin C., Application of The Mediator Design Pattern to Monte Carlo Simulation in Genetic Epidemiology, Masters Thesis, Case Western Reserve University, Aug. 2008.

Notice of Allowance, U.S. Appl. No. 17/958,665, dated Feb. 10, 2023.

Office Action, U.S. Appl. No. 17/880,566, dated Oct. 6, 2022.

Office Action, U.S. Appl. No. 17/880,566, dated Feb. 14, 2023.

Office Action, U.S. Appl. No. 17/958,665, dated Dec. 29, 2022.

Office Action, U.S. Appl. No. 17/989,388, dated Feb. 7, 2023.

Rajeevan, et al. ALFRED: An Allele Frequency Database for Microevolutionary Studies. Evolutionary Bioinformatics Online (2005) vol. 1, p. 1-10.

Roberson, E., Examining Copy Number Alterations, Unexpected Relationships and Population Structure Using SNPs, Johns Hopkins University, Baltimore, MD. Jul. 2009.

Roberson, Elisha D. O. et al., Visualization of Shared Genomic Regions and Meiotic Recombination in High-Density SNP Data, PLoS One 4(8): e6711. doi:I 0.1371/journal.pone.0006711 (Aug. 21, 2009).

*23andme, Inc., v. Ancestry.com DNA, LLC, Ancestry.com Operations Inc., Ancestry.com LLC*, No. 2019-1222, United States Court of Appeals for the Federal Circuit, On Petition for Rehearing En Banc; Order, denied; filed Jan. 9, 2020, Case No. 18-cv-02791-EMC, pp. 1-2.

*23andme, Inc., v. Ancestry.com DNA, LLC, Ancestry.com Operations Inc., Ancestry.com LLC*, No. 2019-1222, United States Court

(56) References Cited

OTHER PUBLICATIONS of Appeals for the Federal Circuit, Petition for Rehearing En Banc, filed Nov. 4, 2019, Case No. 18-cv-02791-EMC, pp. 1-28.
23andme, Inc., v. Ancestry.com DNA, LLC, Ancestry.com Operations Inc., Ancestry.com LLC, No. 2019-1222, United States Court of Appeals for the Federal Circuit, Defendant's-Appellees' Response to Appellant 23andme, Inc.'s Petition for Rehearing En Banc, filed Dec. 19, 2019, Case No. 18-cv-02791-EMC, pp. 1-25.
Abbas et al. "A wide variety of mutation in the parkin gene are responsible for autosomal recessive parkinsonism in Europe", Hum. Mol. Genet., vol. 8, No. 4 (1999) pp. 567-574.
Abe, et al., Implementing an Integrated Time-Series Data Mining Environment Based on Temporal Pattern Extraction Methods: A Case Study of an Interferon Therapy Risk Mining for Chronic Hepatitis, 2006, New Frontiers in Artificial Intelligence, Lecture Notes in Computer Science, vol. 4012/2006, pp. 425-435.
Abecasis, et al., "Extent and distribution of linkage disequilibrium in three genomic regions" Am. J. Hum. Genet. 68, (2001) pp. 191-197.
Abecasis, et al., "GOLD—Graphical overview of linkage disequilibrium" Bioinformatics, vol. 16, No. 2, (2000) pp. 182-183.
Abecasis, et al., "GRR: graphical representation of relationship errors" Bioinformatics 17, (2001) pp. 742-743.
Abecasis, et al., "Handling marker-marker linkage disequilibrium: pedigree analysis with clustered markers" Am. J. Hum. Genet. 77 (2005) pp. 754-767.
Abecasis, et al., "Linkage disequilibrium: ancient history drives the new genetics" Hum. Hered. 59, (2005) pp. 118-124.
Abecasis, et al., "MaCH: Using sequence and genotype data to estimate haplotypes and unobserved genotypes" Genetic Epidemiology 34 (2010) pp. 816-834.
Abecasis, et al., "Merlin-rapid analysis of dense genetic maps using sparse gene flow trees" Nat. Genet. 2002, 30 (2002) pp. 97-101.
Abney, et al., "Quantitative-Trait Homozygosity and Association Mapping and Empirical Genomewide Significance in Large, Complex Pedigrees: Fasting Serum-Insulin Level in the Hutterites" Am. J. Hum. Genet. 70, (2002) pp. 920-934.
Aekplakorn, W. et al., "A risk score for predicting incident diabetes in the Thai population", Diabetes Care 2006;29, pp. 1872-1877.
Aharon-Peretz J. et al., "Mutations in the glucocerebrosidase gene and Parkinson's disease in Ashkenazi Jews", N. Engl. J. Med. 351 (2004) pp. 1972-1977.
Albers, et al., "Multipoint Approximations of Identity-by-descent probabilities for accurate linkage analysis of distantly related individuals," The American Journal of Human Genetics 82, Mar. 2008, pp. 607-622.
Alexander, et al., "Fast model-based estimation of ancestry in unrelated individuals", Genome Research 19, (2009) pp. 1655-1664.
Almasy, et al. "Multipoint quantitative-trait linkage analysis in general pedigrees" Am. J. Hum. Genet. 62: (1998) pp. 1198-1211.
Almudevar, A., "A Bootstrap Assessment of Variability in Pedigree Reconstruction Based on DNA Markers" Biometrics, vol. 57, Sep. 2001, pp. 757-763.
Almudevar, A., "A simulated annealing algorithm for maximum likelihood pedigree reconstruction" Theoretical Population Biology, vol. 63, (2003) pp. 63-75.
Almudevar, et al., "Estimation of single-generation sibling relationship based on DNA markers" Journal Agricultural Biological, and Environmental Statistics, vol. 4, No. 2, (1999) pp. 136-165.
Alcalay R.N. et al., "Frequency of known mutations in early-onset Parkinson disease: implication for genetic counseling: the consortium on risk for early onset Parkinson disease study" Arch Neural 67, (2010) pp. 1116-1122.
Altshuler et al. "Genetic mapping in human disease" Science 322(5903) (2009) pp. 881-888.
Anderson, Domestic-Animal Genomics: Deciphering the Genetics of Complex Traits, Mar. 2004, Nature.com, vol. 5. pp. 202-212.
Asakura et al., "Global gene expression profiling in the failing myocardium" Circ. J. 73 (2009) pp. 1568-1576.

Browning, et al., "Missing data imputation and haplotype phase inference for genomewide association studies," Human Genetics, vol. 124, Oct. 11, 2008, pp. 439-450.
Druet, Tom, et al., "A Hidden Markov Model Combining Linkage and Linkage Disequilibrium Information for Haplotype Reconstruction and Quantitative Trait Locus Fine Mapping," Genetics vol. 184, No. 3, Jun. 2010, pp. 789-798.
Grunblatt et al., "Gene expression profiling of parkinsonian substantia nigra pars compacta: alterations in ubiquitin-proteasome, heat shock protein, iron and oxidative stress regulated proteins, cell adhesion/cellular matrix and vesicle trafficking genes" J. Neural Transm 111 (12) (2004) pp. 1543-1573.
Hindorff L.A. et al., "Potential etiologic and functional implications of genome-wide association loci for human diseases and traits" Proc Natl Acad Sci USA 106, (2009) pp. 9362-9367.
Hirschhorn J.N., "Genomewide Association Studies-Illuminating Biologic Pathways" N. Engl. J. Med. 360 (2009) pp. 1699-1701.
International Schizophrenia Consortium et al. "Common polygenic variation contributes to risk of schizophrenia and bipolar disorder" Nature 460(7256) (2009) pp. 748-752.
Kim et al. "A multivariate regression approach to association analysis of a quantitative trait network" Bioinformatics 25 (12)(2009) pp. i204-i212.
Mealiffe, et al., "Assessment of Clinical Validity of a Breast Cancer Risk Model Combining Genetic and Clinical Information" J. Natl. Cancer Institute (JNCI), vol. 102, No. 21, Nov. 3, 2010, pp. 1618-1627.
Notice of Allowance, U.S. Appl. No. 17/975,949 dated Mar. 21, 2023.
Notice of Allowance, U.S. Appl. No. 17/989,388, dated Mar. 23, 2023.
Office Action, U.S. Appl. No. 17/975,949, dated Feb. 16, 2023.
Office Action, U.S. Appl. No. 17/980,024, dated Jun. 7, 2023.
Office Action, U.S. Appl. No. 17/989,388, dated Mar. 8, 2023.
Office Action, U.S. Appl. No. 18/099,478, dated Apr. 21, 2023.
Office Action, U.S. Appl. No. 18/191,525, dated Jun. 23, 2023.
Pruim R.J. et al., "LocusZoom: regional visualization of genome-wide association scan results" Bioinformatics 26 (2010) pp. 2336-2337.
Ruderfer, et al., "Family-based genetic risk prediction of multifactorial disease," Genome Medicine, vol. 2:1, Jan. 15, 2010, pp. 1-7. doi:I0.1186/gml23.
Traherne, Jan. 2006, "Genetic analysis of completely sequenced disease-associated MHC haplotypes identifies shuffling of segments in recent human history," PLOS Genetics. pp. 81-92.
U.S. Appl. No. 13/908,455, filed Jun. 3, 2013.
Wu et al. "Genome-wide association analysis by lasso penalized logistic regression," Bioinformatics 25(6) (2009) pp. 714-721.
Longato-Stadler, et al., "Personality Traits and Platelet Monoamine Oxidase Activity in a Swedish Male Criminal Population", Neuropsychobiology, 2002, pp. 202-208,46 (4), S. Karger AG, Basel, Switzerland.
Lotufo et al., "Male pattern baldness and coronary heart disease" Arch. Intern. Med. 160 (2000) pp. 165-171.
Lowe, et al., "Genome-Wide Association Studies in an Isolated Founder Population from the Pacific Island ofKosrae," PLoS Genet 5(2), 2009, eI000365, pp. 1-17. <doi: 10.1371/journal.pgen. 1000365>.
Lucking et al., "Association Between Early-Onset Parkinson's Diseaseand Mutations in the Parkin Gene" N. Engl. J. Med. 342, May 2000, pp. 1560-1567.
Lunceford J.K. and Davidian M., "Stratification and weighting via the propensity score in estimation of causal treatment effects: a comparative study" Stat Med 23, (2004) pp. 2937-2960.
Lynch, et al., "Analysis of population genetic structure with RAPD markers" Molecular Ecology, 3, (1994) pp. 91-99.
Lynch, M., "Estimation of relatedness by DNA fingerprinting" Molecular and Biological Evolution, 5, (1988) pp. 584-599.
Lynch, M., et al., "Estimation of Pairwise Relatedness With Molecular Markers", Genetics 152: 1753-1766 (Aug. 1999).

(56) References Cited

OTHER PUBLICATIONS

Lyssenko, M.D., et al., "Clinical Risk Factors, DNA Variants, and the Development of Type 2 Diabetes" The New England Journal of Medicine, vol. 359, Nov. 20, 2008, pp. 2220-2232. <doi:10.1056/NEJMoa0801869>.

Ma et al., "Polymorphisms of fibroblast growth factor receptor 4 have association with the development of prostate cancer and benign prostatic hyperplasia and the progression of prostate cancer in a Japanese population" Int. J. Cancer 123(11) (2008) pp. 2574-2579.

Ma, et al., "PatternHunter: faster and more sensitive homology search" Bioinformatics, vol. 18, No. 3 (2002) pp. 440-445.

Mani, et al., Causal Discover From Medical Textual Data, Fall 2000, Hanley and Belfus Publishers, pp. 542-546.

Mao, et al., "A Monte Carlo algorithm for computing the IBD matrices using incomplete marker information" Heredity (2005) 94, pp. 305-315.

Marchini, et al., "A comparison of phasing algorithms for trios and unrelated individuals," Am. J. Hum. Genet. 78, 2006, pp. 437-450.

Matsuzaki, et al., "Genotyping over 100,000 SNPs on a pair of oligonucleotide arrays" Nat. Methods, vol. 1, No. 2, Nov. 2004, pp. 109-111.

Matsuzaki, et al., "Parallel genotyping of over 10,000 SNPs using a one-primer assay on a high density oligonucleotide array" Genome Res., vol. 14, No. 3, Mar. 2004, pp. 414-425.

McPeek, et al., "Statistical test for detection of misspecified relationships by use of genome screen data" Am. J. Hum. Genet. 66, (2000) pp. 1076-1094.

Meigs, et al., "Genotype score in addition to common risk factors for prediction of type 2 diabetes" N. Engl. J. Med. 2008; 359: 2208-9.

Meuwissen, et al., "Fine mapping of a quantitative trait locus for twinning rate using combined linkage and linkage disequilibrium mapping," Genetics 161 (2002) pp. 373-379.

Meuwissen, et al., "Multipoint Identity-by-Descent Prediction Using Dense Markers to Map Quantitative Trait Loci and Estimate Effective Population Size," Genetics 176, Aug. 2007, pp. 2551-2560.

Meuwissen, Theo HE, and Mike E. Goddard, "Prediction of identity by descent probabilities from marker-haplotypes", Genetics Selection Evolution 33, No. 6 (2001): 1-30.

Miano, et al., "Pitfalls in homozygosity mapping" Am. J. Hum. Genet. 67, (2000) pp. 1348-1351.

Milligan, Brook G., "Maximum-Likelihood Estimation of Relatedness", Genetics 163: 1153-1167 (Mar. 2003).

Miyamoto, et al., "Diagnostic and Therapeutic Applications of Epigenetics", Japanese Journal of Clinical Oncology, Jun. 1, 2005, pp. 293-301, 35 (6), Keigakul Publishing Company, Japan.

Miyazawa, Hitoshi, Masaaki Kato, Takuya Awata, Masakazu Kohda, Hiroyasu Iwasa, Nobuyuki Koyama, Tomoaki Ranaka, Shunei Kyo, Yasushi Okazaki, and Koichi Hagiwara, "Homozygosity haplotype allows a genomewide search or the autosomal segments shared among patients", The American Journal of Human Genetics 80, No. 6 (2007): 1090-1102.

Morris, et al., "The avuncular index and the incest index" Advances in Forensic Haemogenetics 2, (1988) pp. 607-611.

Morrison, A. C., et al. "Prediction of Coronary Heart Disease Risk using a Genetic Risk Score: The Atherosclerosis Risk in Communities Study," American Journal of Epidemiology, vol. 166, No. 1, Apr. 18, 2007, pp. 28-35.

Morton, N.E., "Sequential test for the detection of linkage" Am. J. Hum. Genet. 7 (1955) pp. 277-318.

Motro, et al., "The affected sib method. I. Statistical features of the affected sib-pair method" Genetics 110, (1985) pp. 525-538.

Nadkarni, Prakash M., et al. "Data Extraction and Ad Hoc Query of an Entity-Attribute-Value Database", Journal of the American Medical Informatics Association, vol. 5, No. 6, Nov./Dec. 1998, pp. 511-527.

NCBI Reference SNP Cluster Report: rs10513789_ Nov. 2003_
NCBI Reference SNP Cluster Report: rs10513789, Nov. 2003, pp. 1-6. [Retrieved from the internet, May 2, 2011] <URL:http://www.ncbi.nlm.nih.gov/projects/SNP/snp_ref_cgi?rs=10513789>.

Nelson et al., "The program of androgen-responsive genes in neoplastic prostate epithelium", Proc. Natl. Acad. Sci., vol. 99. No. 18, Sep. 2002, pp. 11890-11895.

Nelson, et al., "Genomic mismatch scanning: A new approach to genetic linkage mapping" Nature Genetics, vol. 4, May 1993, pp. 11-18.

Newton, et al., "Inferring the location and effect of tumor suppressor genes by instability selection modeling of allelic-loss data" Biometrics 56, (2000) pp. 1088-1097.

Newton, et al., "On the statistical analysis of allelic-loss data" Statistics in Medicine 17, (1998) pp. 1425-1445.

Nielsen, T. et al. Molecular characterisation of soft tissue tumours: a gene expression study. The Lancet 359, 1301-1307 (2002).

Ning et al., "SSAHA: A Fast Search Method for Large DNA Databases," Cold Spring Harbor Laboratory Press, 2001.

Notice of Allowance, U.S. Appl. No. 12/644,791, dated Feb. 25, 2013.

Notice of Allowance, U.S. Appl. No. 15/664,619, dated Aug. 19, 2020.

Notice of Allowance, U.S. Appl. No. 15/927,785, dated Jul. 30, 2020.

Notice of Allowance, U.S. Appl. No. 15/927,785, dated Sep. 2, 2020.

Notice of Allowance, U.S. Appl. No. 15/999,198, dated Feb. 24, 2021.

Notice of Allowance, U.S. Appl. No. 16/151,721, dated Jun. 23, 2022.

Notice of Allowance, U.S. Appl. No. 16/151,721, dated Oct. 13, 2022.

Notice of Allowance, U.S. Appl. No. 16/519,295, dated Jan. 13, 2021.

Notice of Allowance, U.S. Appl. No. 17/004,494, dated Feb. 4, 2021.

Notice of Allowance, U.S. Appl. No. 17/004,911, dated Dec. 11, 2020.

Notice of Allowance, U.S. Appl. No. 17/073,095, dated Jan. 21, 2021.

Notice of Allowance, U.S. Appl. No. 17/073,110, dated Apr. 29, 2021.

Almudevar, et al., "Most powerful permutation invariant tests for relatedness hypotheses based on genotypic data" Biometrics 57, Dec. 2001, pp. 1080-1088.

Altschul, et al. "Basic Local Alignment Search Tool" J. Mol. Biol. (1990) 215, pp. 403-410.

Amorim, et al., "Pros and cons in the use of SNP's in forensic kinship investigation: a comparative analysis with STRs" Forensic Sci. Int. 150, (2005) pp. 17-21.

Amos and Elston, "Robust Methods for the Detection of Genetic Linkage for Quantitative Data From Pedigree" Genetic Epidemiology 6, (1989) pp. 349-360.

Amos, et al., "The Probabilistic Determination of Identity-by-Descent Sharing for Pairs of Relatives from Pedigrees" Am. J. Hum. Genet. 47 (1990) pp. 842-853.

Anderson, Amy D., et al., "A Maximum-Likelihood Method for the Estimation of Pairwise Relatedness in Structured Populations", Genetics 176: 421-440 (May 2007).

Anonymous, "Frequency" (Web Definition), Feb. 24, 2011, Wikipedia.

Ayers, et al. "Reconstructing Ancestral Haplotypes with a Dictionary Model" Department of Statistics Papers, Department of Statistics, UCLA, UC Los Angeles, Mar. 28, 2005, pp. 1-41.

Bacolod, et al., "The Signatures of Autozygosity among Patients with Colorectal Cancer" Cancer Res. vol. 68, No. 8, Apr. 15, 2008, pp. 2610-2621.

Balding, et al., "A method for quantifying differentiation between populations at multi-allelic loci and its implications for investigating identity and paternity" Genetica, 96 (1995) pp. 3-12.

Balkau, B. et al. "Predicting diabetes: clinical, biological, and genetic approaches: data from the Epidemiological Study on the Insulin Resistance Syndrome {DESIR}", Diabetes Care 31:10 (2008) pp. 2056-2061.

(56) References Cited

OTHER PUBLICATIONS

Ballantyne, J., "Mass disaster genetics" Nature Genet. 15, (1997) pp. 329-331.
Batzoglou, Serafim, Lior Pachter, Jill P. Mesirov, et al. "Human and Mouse Gene Structure: Comparative Analysis and Application to Exon Prediction." Genome Research. 2000 10: 950-958. Copyright 2000, Cold Spring Harbor Laboratory Press.
Belkhir, et al., "IDENTIX, a software to test for relatedness in a population using permutation methods" Molecular Ecology, 2, (2002) pp. 611-614.
Bickel et al., "Discriminative learning for differing training and test distributions", 2007 Proceeding of the 24th International conference on machine learning, Corvallis, OR 2007 pp. 81-89.
Bickel, J.E., "Some Comparisons among Quadratic, Spherical, and Logarithmic Scoring Rules" Decision Analysis, vol. 4, No. 2, Jun. 2007, pp. 49-65.
Bieber, et al., "Finding criminals through DNA of their relatives" Science 312, (2006) pp. 1315-1316.
Bit-level parallelism definition Wikipedia.com, (2021) p. 1. downloaded Apr. 14, 2021.
Blackwell, et al., "Identity by Descent Genome Segmentation Based on Single Nucleotide Polymorphism Distributions," Institute for Biomedical Computing, Washington University in St. Louis, Jan. 31, 1999.
Blouin, M.S. et al., "Use of microsatellite loci to classify individuals by relatedness" Molecular Ecology, vol. 5, (1996) pp. 393-401.
Blouin, Michael S., "DNA-based methods for pedigree reconstruction and kinship analysis in natural populations", Trends in Ecology & Evolution 18, No. 10 (2003): 503-511.
Boehnke, et al., "Accurate Inference of Relationships in Sib-Pair Linkage Studies" Am. J. Hum. Genet. 61, (1997) pp. 423-429.
Boehnke, M., "Allele frequency estimation from data on relatives" Am. J. Hum. Genet. 48, (1991) pp. 22-25.
Bonifati V. et al., "Mutations in the DJ-1 gene associated with autosomal recessive early-onset parkinsonism" Science 299 (2003), pp. 256-259.
Borsting et al. "Performance of the SNPforID 52 SNP-plex assay in paternity testing," (Forensic Science International, vol. 2 (2008) pp. 292-300.
Brenner, C.H. "Kinship Analysis by DNA When There Are Many Possibilities" Progress in Forensic Genetics, vol. 8, (2000) pp. 94-96, Elsevier Science.
Brenner, C.H., "Issues and strategies in the DNA identification of World Trade Center victims" Theor. Popul. Biol. 63, (2003) pp. 173-178.
Brenner, C.H., "Symbolic kinship program" Genetics, 145, (1997) pp. 535-542.
Brief for Defendants—Appellees Ancestry.com DNA, LLC, Ancestry.com Operations Inc., nd Ancestry.com LLC, Case No. 2019-1222, Document: 24, Filed on Mar. 18, 2019, in the US Court of Appeals for the Federal Circuit, pp. 1-76.
Brief of Appellant 23AndMe, Inc., Case No. 2019-1222, Document 19, Filed on Feb. 4, 2019, in the US Court of Appeals for the Federal Circuit, pp. 1-140.
Broman, et al., "Estimation of pairwise relationships in the presence of genotyping errors" Am. J. Hum. Genet. 63, (1998) pp. 1563-1564.
Broman, et al., "Long Homozygous Chromosomal Segments in Reference Families from the Centre d'E'tude du Polymorphisme Humain" Am. J. Hum. Genet. 65, (1999) pp. 1493-1500.
Browning, Brian L., and Sharon R Browning, "Efficient multilocus association testing for whole genome association 42 studies using localized haplotype clustering", Genetic Epidemiology: The Official Publication of the International Genetic Epidemiology Society 31, No. 5 (2007): 365-375.
Browning, et al., "A unified approach to Genotype imputation and Haplotype-Phase inference for large data sets of Trios and unrelated individuals" Am. J. Hum. Genet. 84, (2009) pp. 210-223.
Browning, et al., "On reducing the statespace of hidden markov models for the identity by descent process" Theor. Popul. Biol. 62, (2002) pp. 1-8.
Browning, Sharon R, and Brian L. Browning, "Rapid and accurate haplotype phasing and missing-data inference for whole-genome association studies by use of localized haplotype clustering," The American Journal of Human Genetics, No. 5 (2007): 1084-1097.
Browning, Sharon R., "Estimation of pairwise identity by descent from dense genetic marker data in a population sample of haplotypes", Genetics 178, No. 4 (2008): 2123-2132.
Cannings, C., "The identity by descent process along the chromosome" Human Heredity, 56 (2003) pp. 126-130.
Carlson et al., "Selecting a Maximally Informative Set of Single Nucleotide Polymorphisms for Association Analyses Using Linkage Disequilibrium", Am. J. Hum. Genet. 74 (2004) pp. 106-120.
Carlson, et al., "Mapping complex disease loci in whole-genome association studies" Nature 429 (2004) pp. 446-452.
Carson, et al., Abnormal Psychology and Modern Life, 8th edition, 1988, pp. 56-57, Scott Foresman and Company, Glenview, IL, USA.
Castets et al., "Zinedin, SG2NA, and striatin are calmodulin-binding, WO repeat proteins principally expressed in the brain", J. Biol. Chem. 275, (2000) pp. 19970-19977.
Catalano et al., "Mifepristone induced progesterone withdrawal reveals novel regulatory pathways in human endometrium", Mol. Hum. Reprod. 13(9) (2007) pp. 641-654.
Cavalli-Sforza, L., "The Human Genome Diversity Project: past, present and future," Nature Reviews, Genetics, vol. 6, Apr. 2005, pp. 333-340.
Cespivova, et al., Roles of Medical Ontology in Association Mining CRISP-DM Cycle, Proceedings of the ECML/PKDD04 Workshop on Knowledge Discovery and Ontologies, PISA 2004.
Chapman, et al., "The effect of population history on the lengths of ancestral chromosome segments" Genetics, 162, Sep. 2002, pp. 449-458.
Chen, et al., "Robust relationship inference in genome-wide association studies", Bioinformatics 26 No. 22, 2010, pp. 2867-2873.
Chen, Wei-Min, and Goncalo R. Abecasis, "Family-Based Association Tests for Genomewide Association Scans," The American Journal of Human Genetics, vol. 81, Nov. 2007.
Cheung, et al., "Linkage-disequilibrium mapping without genotyping" Nature Genetics 18, (1998) pp. 225-230.
Gneiting, T. et al., "Probabilistic forecasts, calibration and sharpness" Hal-00363242 (2007) pp. 1-28. <URL:https://hal.archives-ouvertes.fr/hal-00363242>.
Goodnight, et al., "Computer software for performing likelihood tests of pedigree relationship using genetic markers" Molecular Ecology, vol. 8, (1999) pp. 1231-1234.
Grafen, A., "A geometric view of relatedness" Oxford Surveys in Evolutionary Biology, 2 (1985) pp. 39-89.
Grant, et al., "Significance testing for direct identity-by-descent mapping" Ann. Hum. Genet. 63, (1999) pp. 441-454.
Greenspan, et al., "Model-based inference of haplotype block variation" J. Comput. Biol. 11, (2004) pp. 493-504.
Griffiths, et al., "Ancestral inference of samples of DNA sequences with recombination" Journal of Computational Biology, vol. 3, No. 4 (1996) pp. 479-502.
Guan and Stephens, "Practical issues in imputation-based association mapping" PLoS Genet. 4(12) Dec. 2008, e100279, pp. 1-11.
Gudbjartsson, et al., "Allegro, a new computer program for multipoint linkage analysis" Nat. Genet. 25, (2000) pp. 12-13.
Guo, Sun-Wei, "Proportion of genome shared identical by descent by relatives: concept, computation, and applications", American Journal of Human Genetics 56, No. 6 (1995): 1468.
Gusev, et al., "Whole population, genome-wide mapping of hidden relatedness," Genome Research, vol. 19, 2009, pp. 318-326.
Habuchi et al., "Increased risk of prostate cancer and benign hyperplasia associated with a CYP17 gene polymorphism with a gene dosage effect" Cancer Res. 60(20) (2000) pp. 5710-5713.
Hajnal, J., "Concepts of random mating and the frequency of consanguineous marriages," Proceedings of the Royal Society of London. Series B. Biological Sciences 159, No. 97 4 (1963) pp. 125-177.

(56) References Cited

OTHER PUBLICATIONS

Han, Jiawei; Discovery of Multiple-Level Association Rules from Large Database' 1995; pp. 1-12.
Hardy, O.J., "Estimation of pairwise relatedness between individuals and characterization of isolation-by-distance processes using dominant genetic markers" Molecular Ecology, 12 (2003) pp. 1577-1588.
Harris, D.L., "Genotypic covariances between inbred relatives" Genetics 50, (1964) pp. 1319-1348.
Harvard School of Public Health I Harvard Center for Cancer Prevention , "Your Disease Risk" website for calculating disease risk , 34 exemplary pages submitted including heart disease risk estimation and listings of risk factors, last accessed via the world wide web on Apr. 30, 2007, at the URL address:http://www.yourdiseaserisk.harvard.edu/english/index.htm).
Hauser et al., "A genome-wide scan for early-onset coronary artery disease in 438 families: the GENECARD Study" Am. J. Hum. Genet. 75(3) (2004) pp. 436-447.
Hayward, et al., "Fibrillin-1 mutations in Marfan syndrome and other type-1 fibrillinopathies" Hum. Mutat. 10 (1997) pp. 415-423.
Healy et al. "Phenotype, genotype, and worldwide genetic penetrance of LRRK2-associated Parkinson's disease: a case-control study" Lancet Neurol. 7(7) (2008) pp. 583-590.
Heath, et al., "A novel approach to search for identity by descent in small samples of patients and controls from the same Mendelian breeding unit: a pilot study in myopia" Human Heredity, vol. 52, Feb. 2001, pp. 183-190.
Hepler, A.B., "Improving forensic identification using Bayesian Networks and Relatedness Estimation" Ph.D Thesis, NCSU, Raleigh (2005) pp. 1-131.
Hernandez-Sanchez, et al., "On the prediction of simultaneous inbreeding coefficients at multiple loci" Genet. Res. 83 (2004) pp. 113-120.
Hernandez-Sanchez, et al., "Prediction of IBD based on population history for fine gene mapping" Genet. Sel. Evol. 38 (2006) pp. 231-252.
Heyer, et al., "Variability of the genetic contribution of Quebec population founders associated to some deleterious genes" Am. J. Hum. Genet. 56 (1995) pp. 970-978.
Hill, et al. "Prediction of multilocus identity-by-descent" Genetics 176, Aug. 2007, pp. 2307-2315.
Hill, et al., "Linkage disequilibrium in finite populations" Theor. Appl. Genet. 38, (1968) pp. 226-231.
Hill, et al., "Prediction of multi-locus inbreeding coefficients and relation to linkage disequilibrium in random mating populations" Theor Popul Biol. Sep. 2007, 72(2), pp. 179-185. doi: 10.1016/j.tpb.2006.05.006.
Hill, et al., "Variances and covariances of squared linkage disequilibria in finite populations" Theor. Pop. Biol., 33 (1988) pp. 54-78. [PubMed: 3376052].
Hill, W.G., "Disequilibrium among several linked neutral genes in finite population. II Variances and covariances of disequilibria" Theor. Pop. Biol., vol. 6, 1974, pp. 184-198.
Hillmer et al., "Genetic variation in the human androgen receptor gene is the major determinant of common early-onset androgenetic alopecia" Am. J. Hum. Genet. 77 (2005) pp. 140-148.
Hinrichs, et al., "Multipoint identity-by-descent computations for single-point polymorphism and microsatellite maps," BMC Genet. 6, Dec. 30, 2005, S34. doi:10.1186/1471-2156-6-S1-S34.
Hitsch, et al., "What Makes You Click?—Mate Preference and Matching Outcomes in Online Dating", MIT Sloan Research Paper No. 4603-06, Apr. 2006.
Hoggart et al. "Simultaneous analysis of all SNPs in genome-wide and re-sequencing association studies" PLoS Genet. 4(7) (2008) e1000130.
Hon, et al., "Discovering Distant Relatives within a Diverse Set of Populations Using DNA Segments Identical by Descent" Advancing Human Genetics & Genomics Annual Meeting Poster Session, Oct. 20, 2009, 23andMe, Inc., pp. 1-2.

Houwen, et al., "Genomic screening by searching for shared segments: mapping a gene for benign recurrent intrahepatic cholestasis" Nature Genetics vol. 8, Dec. 1994, pp. 380-386.
Howie, et al., "A Flexible and Accurate Genotype Imputation Method for the Next Generation of Genome-Wide Association Studies," PLoS Genetics, vol. 5, No. 6, Jun. 2009, pp. 1-15.
Hu, X.S., "Estimating the correlation of pairwise relatedness along chromosomes" Heredity 94, (2004) pp. 338-346. [PubMed: 15354191].
Huang, et al. "Whole genome DNA copy number changes identified by high density oligonucleotide arrays," Hum. Genomics vol. 1, No. 4, May 2004, pp. 287-299.
Huang, et al., "Ignoring linkage disequilibrium among tightly linked markers induces false positive evidence of linkage for affected sib pair analysis" Am. J. Hum. Genet. 75, (2004) pp. 1106-1112.
Idury, et al., "A faster and more general hidden Markov model algorithm for multipoint likelihood calculations" Hum. Hered. 47(1997) pp. 197-202.
International HapMap Consortium "A second generation human haplotype map of over 3.1 million SNPs" Nature 449 (764) Oct. 18, 2007, pp. 851-861.
International Search Report, PCT App. No. PCT/US2007/020884, dated Apr. 7, 2009.
International Search Report, PCT App. No. PCT/US2009/006706, dated Mar. 3, 2010.
Ioannidis J.P. et al., "Assessment of cumulative evidence on genetic associations: interim guidelines" Int J Epidemiol 37 (2008) pp. 120-132.
Jacquard, A., "Genetic information given by a relative" Biometrics, 28, (1972) pp. 1101-1114.
Jankovic J., "Parkinson's disease: clinical features and diagnosis" J Neurol Neurosurg Psychiatr 79 (2008) pp. 368-376.
Jaski et al., "Calcium upregulation by percutaneous administration of gene therapy in cardiac disease (CUPID trial), a first-in-human phase 1/2 clinical trial" J. Card. Fail 15(3) (2009) pp. 171-181.
Jenkins et al., "Noninherited risk factors and congenital cardiovascular defects: a scientific statement from the American Heart Association Council on Cardiovascular disease in the Young: endorsed by the American Academy of Pediatrics" Circulation 115(23) (2007) pp. 2995-3014.
Jiang, et al., "An efficient parallel implementation of the hidden Markov methods for genomic sequence-search on a massively parallel system." IEEE Transactions on Parallel and Distributed Systems 19.1 (2008) pp. 15-23.
Notice of Allowance, U.S. Appl. No. 18/099,478, dated Jul. 19, 2023.
Notice of Allowance, U.S. Appl. No. 18/191,525, dated Aug. 22, 2023.
Office Action, U.S. Appl. No. 17/980,024, dated Jul. 28, 2023.
Office Action, U.S. Appl. No. 17/981,917, dated Oct. 16, 2023.
U.S. Appl. No. 60/999,175, filed Oct. 15, 2007.
U.S. Appl. No. 61/070,321, filed Mar. 19, 2008.
Valente E.M. et al., "Hereditary early-0nset Parkinson's disease caused by mutations in PINK1" Science 304 (2004), pp. 1158-1160.
Van De Casteele, et al., "A comparison of microsatellite-based pairwise relatedness estimators" Molecular Ecology 10, (2001) pp. 1539-1549.
Vrbsky, S.V. & Liu, J.W.S. "Approximate—A Query Processor That Produces Monotonically Improving Approximate Answers." IEEE Transactions on Knowledge and Data Engineering 5, 1056-1068 (1993).
Wagner, S.F.,"Introduction to Statistics, Harper Collins Publishers", 1992, pp. 23-30.
Wang, et al., "An estimator of pairwise relatedness using molecular markers" Genetics, vol. 160 (2002) pp. 1203-1215.
Wang, et al., "An integrated hidden Markov model designed for high-resolution copy number variation detection in whole-genome SNP genotyping data," Genome Res. 17, 2007, pp. 665-1674.
Wannamethee, S.G. et al. "Metabolic syndrome vs Framingham Risk Score for prediction of coronary heart disease, stroke, and type 2 diabetes mellitus", Arch. Intern. Med. 2005;165, pp. 2644-2650.

(56) References Cited

OTHER PUBLICATIONS

Weir, et al., "A maximum-likelihood method for the estimation of pairwise relatedness in structured populations" Genetics 176, (2007) DD. 421-440.

Weir, et al., "Allelic association patterns for a dense SNP map" Genetic Epidemiology 24, (2004) pp. 442-450.

Weir, et al., "Behavior of pairs of loci in finite monoecious populations" Theor. Popul. Biol. 6 (1974) pp. 323-354.

Weir, et al., "Estimating F-statistics" Annual Review of Genetics, 36, (2002) pp. 721-750.

Weir, et al., "Genetic relatedness analysis: modern data and new challenges" Nature Genetics 7, (2006) pp. 771-780.

Weir, et al., "Group inbreeding with two linked loci" Genetics 63 (1969) pp. 711-742.

Weir, et al., "Measures of human population structure show heterogeneity among genomic regions" Genome Res. 15 (2005) pp. 1468-1476. [PubMed:16251456].

Weiss, et al., "Association between microdeletion and microduplication at 16p11.2 and autism" New England Journal of Medicine, vol. 358, No. 7, Feb. 14, 2008, pp. 667-675.

Whittemore, et al., "A Class of Tests for Linkage Using Affected Pedigree Members" Biometrics 50, (1994) pp. 118-127.

WHO Expert Consultation, "Appropriate body-mass index for Asian populations and its implications for policy and intervention strategies", Lancet 363, (2004) pp. 157-163.

WHO International Association for the Study of Obesity, International Obesity Task Force, "The Asia-Pacific 29 perspective: Redefining Obesity and its Treatment", Sydney, Australia, Health Communications 2000, pp. 1-56. [PART I].

WHO Technical Report Series 894, "Obesity: preventing and managing the global epidemic", WHO Technical Report Series 894 (2000) pp. 1-253. [Part II].

Wigginton et al., "A note on exact tests of Hardy-Weinberg equilibrium", Am. J. Hum. Genet. 76 (2005) pp. 887-893.

Wijsman, et al., "Multipoint linkage analysis with many multiallelic or dense diallelic markers: Markov chain-Monte Carlo provides practical approaches for genome scans on general pedigrees" Am. J. Hum. Genet. 79, (2006) pp. 846-858.

Wright, S. "Systems of Mating. I. The Biometric Relations Between Parent and Offspring." Genetics, 6:111 (1921).

Yu, et al., "A unified mixed-model method for association mapping accounting for mutiple levels of relatedness" Nature Genet. 38, (2006) pp. 203-208.

Zhang, et al., "A comparison of several methods for haplotype frequency estimation and haplotype reconstruction for tightly linked markers from general pedigrees" Genet. Epidemiol. 30 (2006) pp. 423-437.

Zhao, Hongyu, and Feng Liang, "On Relationship Inference Using Gamete Identity by Descent Data," Journal of Computational Biology, vol. 8, No. 2, 2001.

Zimprich A. et al., "Mutations in LRRK2 cause autosomal-autosomal-dominant parkinsonism with pleomorphic pathology", Neuron 44 (2004) pp. 601-607.

Zou H. and Hastie T., "Regularization and variable selection via the Elastic Net", Journal of the Royal Statistical Society B 67 (2005), pp. 301-320.

Ritland, K., "Marker-inferred relatedness as a tool for detecting heritability in nature" Mol. Ecol. 9, (2000) pp. 1195-1204.

Roddick, et al., Exploratory Medical Knowledge Discover: Experiences and Issues, Jul. 2003, ACM, vol. 5, Issue 1. pp. 94-99.

Sanda, et al., "Genomic analysis I: inheritance units and genetic selection in the rapid discovery of locus linked DNA makers" Nucleic Acids Research, vol. 14, No. 18 (1986) pp. 7265-7283.

Saslow, D. et al., "American Cancer Society Guidelines for Breast Screening with MRI as an Adjunct to Mammography", CA Cancer J. Clin. 57, Mar./Apr. 2007, pp. 75-89.

Schabath, M.B., et al., "Cancer Epidemiology, Biomarkers & Prevention: Combined Effects of the p53 and p73 17 Polymorphisms on Lung Cancer Risk," Cancer Epidemiol. Biomarkers Prev., Jan. 24, 2006, vol. 15, pp. 158-161. doi: 10.1158/1055-9965.EPI-05-0622].

Schaid, et al., "Caution on pedigree haplotype inference with software that assumes linkage equilibrium" Am. J. Hum. Genet. 71, (2002) pp. 992-995.

Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.

Scheuner, et al., "Family History: A Comprehensive Genetic Risk Assessment Method for the Chronic Conditions of Adulthood", American Journal of Medical Genetics, Wiley-Liss, Inc., vol. 71, 1997, pp. 315-324.

Schork, N.J., "Extended Multipoint Identity-by-Descent Analysis of Human Quantitative Traits: Efficiency, Power, and Modeling Considerations" Am. J. Hum. Genet. 53 (1993) pp. 1306-1319.

Schulze, M.B., et al., "An accurate risk score based on anthropometric, dietary, and lifestyle factors to predict the development of type 2 diabetes", Diabetes Care 30:Mar. 3, 2007, pp. 510-515.

Shmulewitz, Dvora, Simon C_ Heath, Maude L. Blundell, Zhihua Han, Ratnendra ShalTTa, Jacqueline Salit, Steven B. Auerbach et al. "Linkage analysis of quantitative traits for obesity, diabetes, hypertension, and dyslipidemia on the Island of Kosrae, Federated States of Micronesia", Proceedings of the National Academy of Sciences 103, No. 10 2006): 3502-3509.

Shore, et al., "A recurrent mutation in the BMP type I receptor ACVR1 causes inherited and sporadic fibrodysplasia pssificans progressiva" Nat. Genet. 38 (2006) pp. 525-527.

Siegmund, et al., "Statistical Analysis of Direct Identity-by-descent Mapping," Annals of Human Genetics (2003) 67,464-470.

Simon-Sanchez J. et al., "Genome-wide SNP assay reveals structural genomic variation, extended homozygosity and cell-line induced alterations in normal individuals", Hum. Mol. Genet. (2007) 16, pp. 1-14.

Slager, et al., "Evaluation of candidate genes in case-control studies: a statistical method to account for related subjects" Am. J. Hum. Genet. 68, (2001) pp. 1457-1462.

Smith, "SNPs and human disease", Nature, 2005, vol. 435, p. 993.

Smouse, et al., "A genetic mixture analysis for use with incomplete source population data" Can J Fisheries Aquatic Sci. 47 (1990) pp. 620-634.

Sobel, et al., "Descent graphs in pedigree analysis: Applications to haplotyping, location scores, and marker-sharing statistics" Am. J. Hum. Genet. 58, (1996) pp. 1323-1337.

Stam, P., "The distribution of the fraction of the genome identical by descent in finite random mating populations" Genet. Res. Camb. 35, (1980) pp. 131-155.

Stephens, et al., "A Comparison of Bayesian Methods for Haplotype Reconstruction from Population Genotype Data," Am. J. Hum. Genet., vol. 73, 2003, pp. 1162-1169.

Stephens, et al., "A New Statistical Method for Haplotype Reconstruction from Population Data," Am. J. Hum. Genet., vol. 68, 2001, pp. 978-989.

Stephens, et al., "Accounting for Decay of Linkage Disequilibrium in Haplotype Inference and Missing-Data Imputation," Am. J. Hum. Genet., vol. 76, 2005, pp. 449-462.

Stem, et al., "Validation of prediction of diabetes by the Archimedes model and comparison with other predicting models", Diabetes Care 31:8, Aug. 2008, pp. 1670-1671.

Stone, et al., "DELRIOUS: a computer program designed to analyze molecular marker data and calculate delta and relatedness estimates with confidence" Molecular Ecology Notes, vol. 1, (2001) pp. 209-212.

Sveinbjomsdottir S., et al., "Familial aggregation of Parkinson's disease in Iceland", N. Engl. J. Med. 343 (2000) pp. 1765-1770.

Tang, Hua, et al., "Estimation of Individual Admixture: Analytical and Study Design Considerations", Genetic Epidemiology 28: 289-301 (2005).

Tanner C.M. et al., "Parkinson disease in twins: an etiologic study" JAMA 281 (1999) pp. 341-346.

Te Meerman, et al., "Genomic Sharing Surrounding Alleles Identical by Descent: Effects of Genetic Drift and Population Growth" Genetic Epidemiology vol. 14 (1997) pp. 1125-1130.

(56) References Cited

OTHER PUBLICATIONS

Teo, et al., "Singapore Genome Variation Project: A haplotype map of three Southeast Asian populations" Genome Res. 19, (2009) pp. 2154-2162.

The International HapMap Consortium, "A haplotype map of the human genome" vol. 437, Oct. 27, 2005, pp. 1300-1320. doi:10.1038/nature04226.

The International HapMap Consortium, "A second generation human haplotype map of over 3.1 million SNPs," Nature, vol. 449, Oct. 18, 2007, pp. 851-860. <doi: 10.1038/nature06258>.

Thomas, Alun, Nicola J. Camp, James M. Farnham, Kristina Allen-Brady, and Lisa A Cannon-Albright, "Shared genomic segment analysis: Mapping disease predisposition genes in extended pedigrees using SNP genotype assays", Annals of human genetics 72, No. 2 (2008): 279-287.

Thomas, et al., "Genomic mismatch scanning in pedigrees" IMA Journal of Mathematics Applied in Medicine and Biology, vol. 11, (1994) pp. 1-16.

Thomas, et al., "Multilocus linkage analysis by blocked Gibbs sampling" Statistics and Computing, vol. 10, (2000), pp. 259-269.

Thompson, E.A., "Estimation of relationships from genetic data", Handbook of statistics 8 (1991), pp. 255-269.

Thompson, E.A., "Inference of genealogical structure" Soc. Sci. Inform. 15, (1976) pp. 477-526.

Thompson, E.A., "The estimation of pairwise relationships" Ann. Hum. Genet., Lond. 39, (1975) pp. 173-188.

Thompson, et al., "The IBD process along four chromosomes," Theor. Popul. Biol. May 73(3) May 2008, pp. 369-373.

Tishkoff, et al., "The Genetic Structure and History of Africans and African Americans," Science, vol. 324(5930), May 22, 2009, pp. 1035-1044. doi:10.1126/science.1172257.

Todorov, et al., "Probabilities of identity-by-descent patterns in sibships when the parents are not genotyped" Genet. Epidemiol. 14 (1997) pp. 909-913.

Transcript of Proceedings dated Jun. 29, 2018, Case No. 18-cv-02791-JCS, Re Defendant's Motion to Dismiss, heard in the United States District Court in and for the Northern District of California LLC, in the matter of *23andMe, Inc.* v. *Ancestry.com DNA, LLC, Ancestry.com Operations Inc.*, and *Ancestry.com*.

Trial Investigators, et al., "DREAM {Diabetes Reduction Assessment with ramipril and rosilglitazone Medication)—Effect of rosiglitazone on the frequency of diabetes in patients with impaired glucose tolerance or impaired fasting glucose: a randomised controlled trial," Lancet 368, (2006) pp. 1096-1105.

Tu, et al., "The maximum of a function of a Markov chain and application to linkage analysis" Adv. Appl. Probab. 31, (1999) pp. 510-531.

Tuomilehto, J. et al., "Prevention of Type 2 diabetes mellitus by changes in lifestyle among subjects with impaired glucose tolerance", N. Engl. J. Med. 344:18, May 3, 2001, pp. 1343-1350.

Tzeng, et al., "Determination of sibship by PCR-amplified short tandem repeat analysis in Taiwan" Transfusion 40, (2000) pp. 840-845.

U.S. Appl. No. 60/895,236, filed Mar. 16, 2007.
U.S. Appl. No. 60/999,064, filed Oct. 10, 2007.
U.S. Appl. No. 60/999,065, filed Oct. 15, 2007.
U.S. Appl. No. 60/999,148, filed Oct. 10, 2007.

* cited by examiner

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| MAKE CONTACT | 4TH COUSIN | 4TH TO 10TH COUSIN | FEMALE MATERNAL HAPLOGROUP F3 | 0.19% | 2 |
| MAKE CONTACT | 5TH COUSIN | 3RD TO 10TH COUSIN | FEMALE CENTRAL ASIAN ANCESTRY MATERNAL HAPLOGROUP G | 0.12% | 1 |
| MAKE CONTACT | 5TH COUSIN | 3RD TO 10TH COUSIN | MALE MATERNAL HAPLOGROUP G1A PATERNAL HAPLOGROUP B1b1b2a1a2d | 0.11% | 1 |
| MAKE CONTACT | 5TH COUSIN | 4TH TO 10TH COUSIN | MALE MATERNAL HAPLOGROUP R9b PATERNAL HAPLOGROUP O3a3c | 0.10% | 1 |
| MAKE CONTACT | 5TH COUSIN | 4TH TO 10TH COUSIN | FEMALE MATERNAL HAPLOGROUP B | 0.09% | 1 |
| MAKE CONTACT | 5TH COUSIN | 4TH TO 10TH COUSIN | MALE MATERNAL HAPLOGROUP D4c1 PATERNAL HAPLOGROUP O3a | 0.09% | 1 |
| MAKE CONTACT | 5TH COUSIN | 4TH TO 10TH COUSIN | MALE MATERNAL HAPLOGROUP F1a1* PATERNAL HAPLOGROUP O1a1* | 0.09% | 1 |
| SHARING GENOMES SEND A MESSAGE | PARENT OR CHILD | -- | ****** MATERNAL HAPLOGROUP C | 50.11% | 24 |

FIG. 4C

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| THIS PERSON WOULD LIKE TO CONTACT YOU. VIEW MESSAGE | AUNT/UNCLE NEPHEW, NIECE OR HALF-SLIBLING | -- | DANIEL LAWRENCE RF2_, MATERNAL HAPLOGROUP U5a1* PATERNAL HAPLOGROUP R1b1b2a1a2d3* | 20.22% | 43 |
| CONTACT ACCEPTED SEND A MESSAGE VIEW CONVERSATION | SIBLING | -- | ERIN LAWRENCE RF2_, MATERNAL HAPLOGROUP H1 | 46.75% | 29 |

FIG. 4H

```
Alice  A G T | C T G | C A A | ...  -- 902
       C G A | C A G | T C A | ...  -- 904

Bob    C A T | G A C | C C G | ...  -- 906
       A A T | C T G | C A A | ...  -- 908
```

FIG. 9

FINDING RELATIVES IN A DATABASE

CROSS-REFERENCE TO RELATED APPLICATIONS

This application is a continuation of and claims priority to U.S. patent application Ser. No. 17/576,738, filed Jan. 14, 2022.

U.S. patent application Ser. No. 17/576,738 is a continuation of and claims priority to U.S. patent application Ser. No. 17/351,052, filed Jun. 17, 2021.

U.S. patent application Ser. No. 17/351,052 is a continuation of and claims priority to U.S. patent application Ser. No. 17/073,110, filed Oct. 16, 2020.

U.S. patent application Ser. No. 17/073,110 is a continuation of and claims priority to U.S. patent application Ser. No. 16/129,645, filed Sep. 12, 2018.

U.S. patent application Ser. No. 16/129,645 is a continuation of and claims priority to U.S. patent application Ser. No. 15/264,493, filed Sep. 13, 2016.

U.S. patent application Ser. No. 15/264,493 is a continuation of and claims priority to U.S. patent application Ser. No. 13/871,744, filed Apr. 26, 2013.

U.S. patent application Ser. No. 13/871,744 is a continuation of and claims priority to U.S. patent application Ser. No. 12/644,791, filed Dec. 22, 2009.

U.S. patent application Ser. No. 12/644,791 is a continuation of and claims priority to U.S. provisional patent application No. 61/204,195, filed Dec. 31, 2008.

All of these cited priority applications are hereby incorporated by reference in their entirety.

BACKGROUND OF THE INVENTION

Genealogy is the study of the history of families and the line of descent from ancestors. It is an interesting subject studied by many professionals as well as hobbyists. Traditional genealogical study techniques typically involve constructing family trees based on surnames and historical records. As gene sequencing technology becomes more accessible, there has been growing interest in genetic ancestry testing in recent years.

Existing genetic ancestry testing techniques are typically based on deoxyribonucleic acid (DNA) information of the Y chromosome (Y-DNA) or DNA information of the mitochondria (mtDNA). Aside from a small amount of mutation, the Y-DNA is passed down unchanged from father to son and therefore is useful for testing patrilineal ancestry of a man. The mtDNA is passed down mostly unchanged from mother to children and therefore is useful for testing a person's matrilineal ancestry. These techniques are found to be effective for identifying individuals that are related many generations ago (e.g., 10 generations or more), but are typically less effective for identifying closer relationships. Further, many relationships that are not strictly patrilineal or matrilineal cannot be easily detected by the existing techniques.

BRIEF DESCRIPTION OF THE DRAWINGS

Various embodiments of the invention are disclosed in the following detailed description and the accompanying drawings.

FIGS. 4A-4I are screenshots illustrating user interface examples in connection with process 300.

FIG. 9 is a diagram illustrating an example in which phased data is compared to identify IBD.

DETAILED DESCRIPTION

Figure 1:
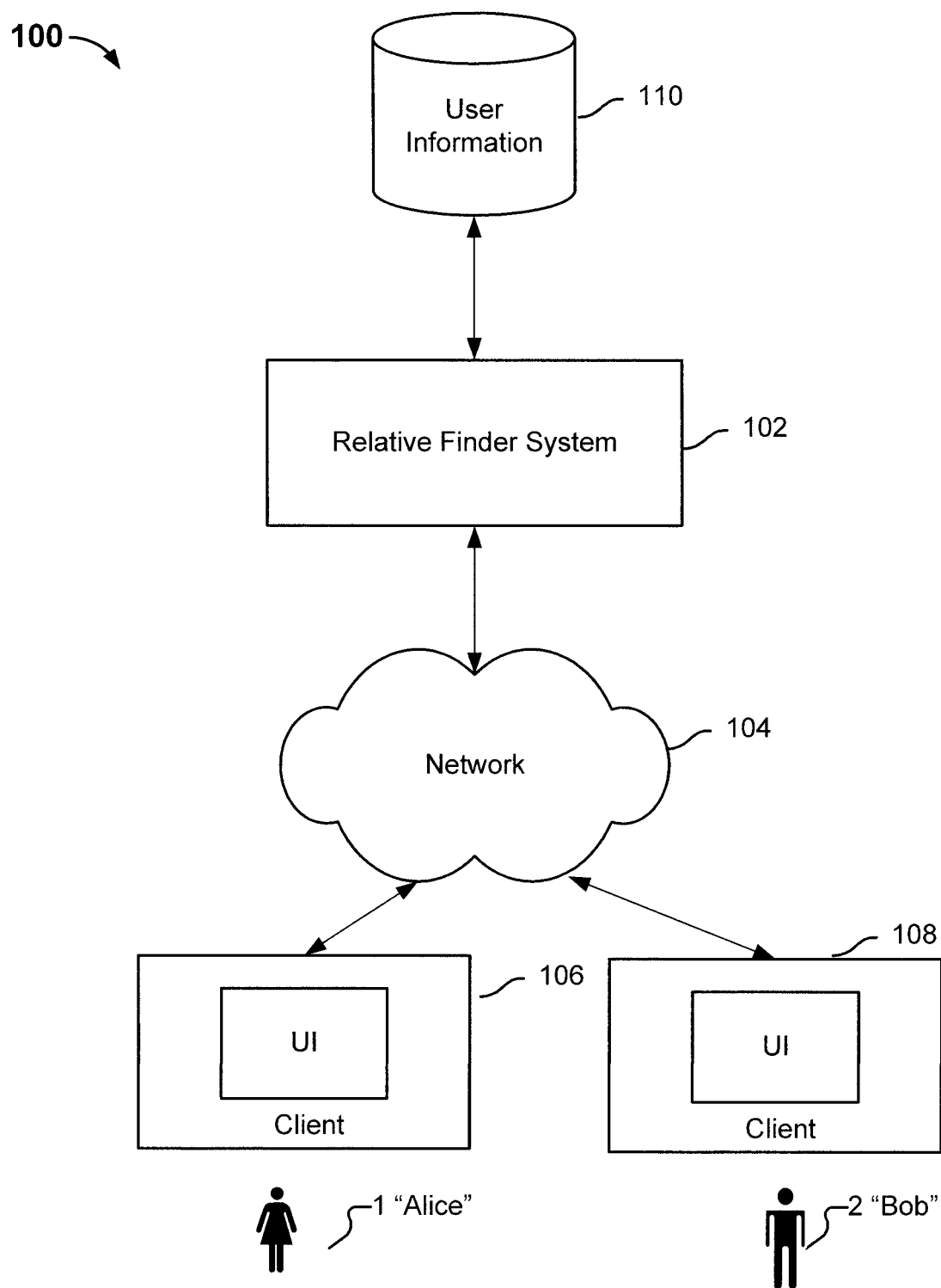
FIG. 1 is a block diagram illustrating an embodiment of a relative finding system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Because of recombination and independent assortment of chromosomes, the autosomal DNA and X chromosome DNA (collectively referred to as recombinable DNA) from the parents is shuffled at the next generation, with small amounts of mutation. Thus, only relatives will share long stretches of genome regions where their recombinable DNA is completely or nearly identical. Such regions are referred to as "Identical by Descent" (IBD) regions because they arose from the same DNA sequences in an earlier generation. The relative finder technique described below is based at least in part on locating IBD regions in the recombinable chromosomes of individuals.

In some embodiments, locating IBD regions includes sequencing the entire genomes of the individuals and comparing the genome sequences. In some embodiments, locating IBD regions includes assaying a large number of markers that tend to vary in different individuals and comparing the markers. Examples of such markers include Single Nucleotide Polymorphisms (SNPs), which are points along the genome with two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Long stretches of DNA sequences from different individuals' genomes in which markers in the same locations are the same or at least compatible indicate that the rest of the sequences, although not assayed directly, are also likely identical.

FIG. 1 is a block diagram illustrating an embodiment of a relative finding system. In this example, relative finder system 102 may be implemented using one or more server computers having one or more processors, one or more special purpose computing appliances, or any other appropriate hardware, software, or combinations thereof. The operations of the relative finder system are described in greater detail below. In this example, various users of the system (e.g., user 1 ("Alice") and user 2 ("Bob")) access the relative finder system via a network 104 using client devices such as 106 and 108. User information (including genetic information and optionally other personal information such as family information, population group, etc.) pertaining to the users is stored in a database 110, which can be implemented on an integral storage component of the relative finder system, an attached storage device, a separate storage device accessible by the relative finder system, or a combination thereof. Many different arrangements of the physical components are possible in various embodiments. In various embodiments, the entire genome sequences or assayed DNA markers (SNPs, STRs, CNVs, etc.) are stored in the database to facilitate the relative finding process. For example, approximately 650,000 SNPs per individual's genome are assayed and stored in the database in some implementations.

System 100 shown in this example includes genetic and other additional non-genetic information for many users. By comparing the recombinable DNA information to identify IBD regions between various users, the relative finder system can identify users within the database that are relatives. Since more distant relationships (second cousins or further) are often unknown to the users themselves, the system allows the users to "opt-in" and receive notifications about the existence of relative relationships. Users are also presented with the option of connecting with their newly found relatives.

Figure 2:
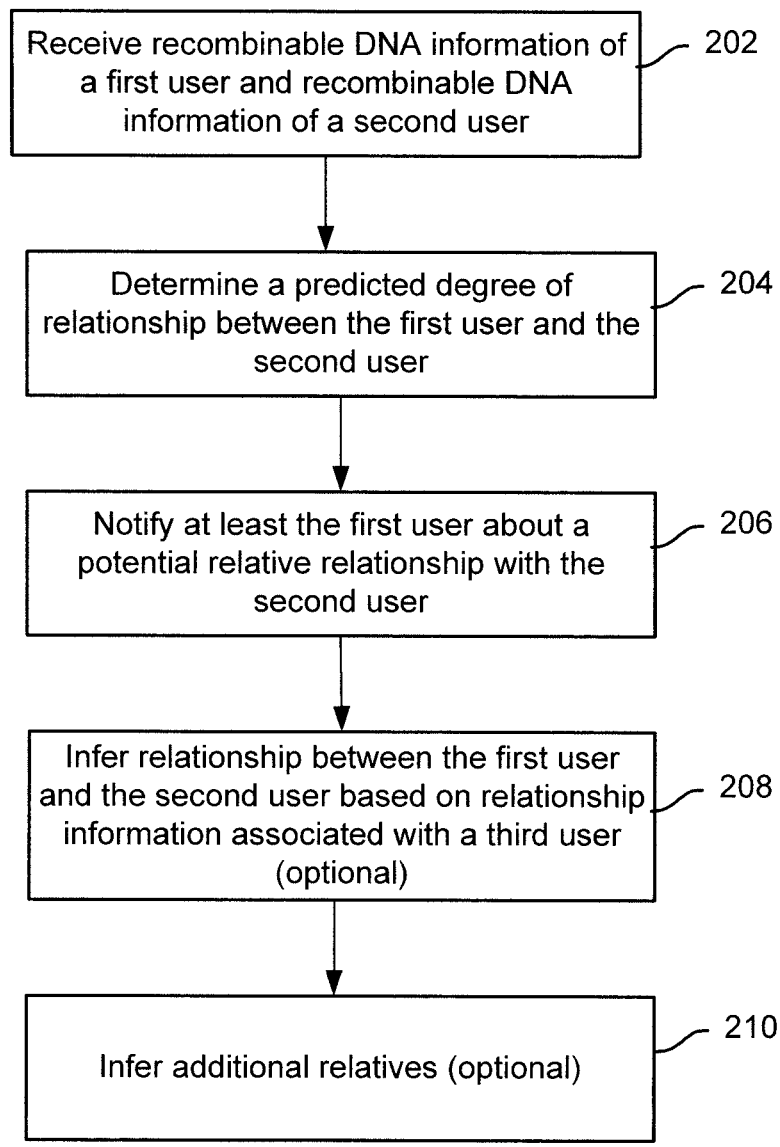
FIG. 2 is a flowchart illustrating an embodiment of a process for finding relatives in a relative finding system.

FIG. 2 is a flowchart illustrating an embodiment of a process for finding relatives in a relative finding system. Process 200 may be implemented on a relative finder system such as 100. The process may be invoked, for example, at a user's request to look for potential relatives this user may have in the database or by the system to assess the potential relationships among various users. At 202, recombinable DNA information of a first user (e.g., Alice) and of a second user (e.g., Bob) is received. In some embodiments, the information is retrieved from a database that stores recombinable DNA information of a plurality of users as well as any additional user information. For purposes of illustration, SNP information is described extensively in this and following examples. Other DNA information such as STR information and/or CNV information may be used in other embodiments.

At 204, a predicted degree of relationship between Alice and Bob is determined. In some embodiments, a range of possible relationships between the users is determined and a prediction of the most likely relationship between the users is made. In some embodiments, it is optionally determined whether the predicted degree of relationship at least meets a threshold. The threshold may be a user configurable value, a system default value, a value configured by the system's operator, or any other appropriate value. For example, Bob may select five generations as the maximum threshold, which means he is interested in discovering relatives with whom the user shares a common ancestor five generations or closer. Alternatively, the system may set a default value minimum of three generations, allowing the users to by default find relatives sharing a common ancestor at least three generations out or beyond. In some embodiments, the system, the user, or both, have the option to set a minimum threshold (e.g., two generations) and a maximum threshold (e.g., six generations) so that the user would discover relatives within a maximum number of generations, but would not be surprised by the discovery of a close relative such as a sibling who was previously unknown to the user.

At 206, Alice or Bob (or both) is notified about her/his relative relationship with the other user. In some embodiments, the system actively notifies the users by sending messages or alerts about the relationship information when it becomes available. Other notification techniques are possible, for example by displaying a list or table of users that are found to be related to the user. Depending on system settings, the potential relatives may be shown anonymously for privacy protection, or shown with visible identities to facilitate making connections. In embodiments where a threshold is set, the user is only notified if the predicted degree of relationship at least meets the threshold. In some embodiments, a user is only notified if both of the user and the potential relative have "opted in" to receive the notification. In various embodiments, the user is notified about certain personal information of the potential relative, the predicted relationship, the possible range of relationships, the amount of DNA matching, or any other appropriate information.

In some embodiments, at 208, the process optionally infers additional relationships or refines estimates of existing relationships between the users based on other relative relationship information, such as the relative relationship information the users have with a third user. For example, although Alice and Bob are only estimated to be $6^{th}$ cousins after step 204, if among Alice's relatives in the system, a third cousin, Cathy, is also a sibling of Bob's, then Alice and Bob are deemed to be third cousins because of their relative relationships to Cathy. The relative relationships with the third user may be determined based on genetic information and analysis using a process similar to 200, based on non-genetic information such as family tree supplied by one of the users, or both.

In some embodiments, the relatives of the users in the system are optionally checked to infer additional relatives at 210. For example, if Bob is identified as a third cousin of Alice's, then Bob's relatives in the system (such as children, siblings, possibly some of the parents, aunts, uncles, cousins, etc.) are also deemed to be relatives of Alice's. In some embodiments a threshold is applied to limit the relationships within a certain range. Additional notifications about these relatives are optionally generated.

Figure 3:
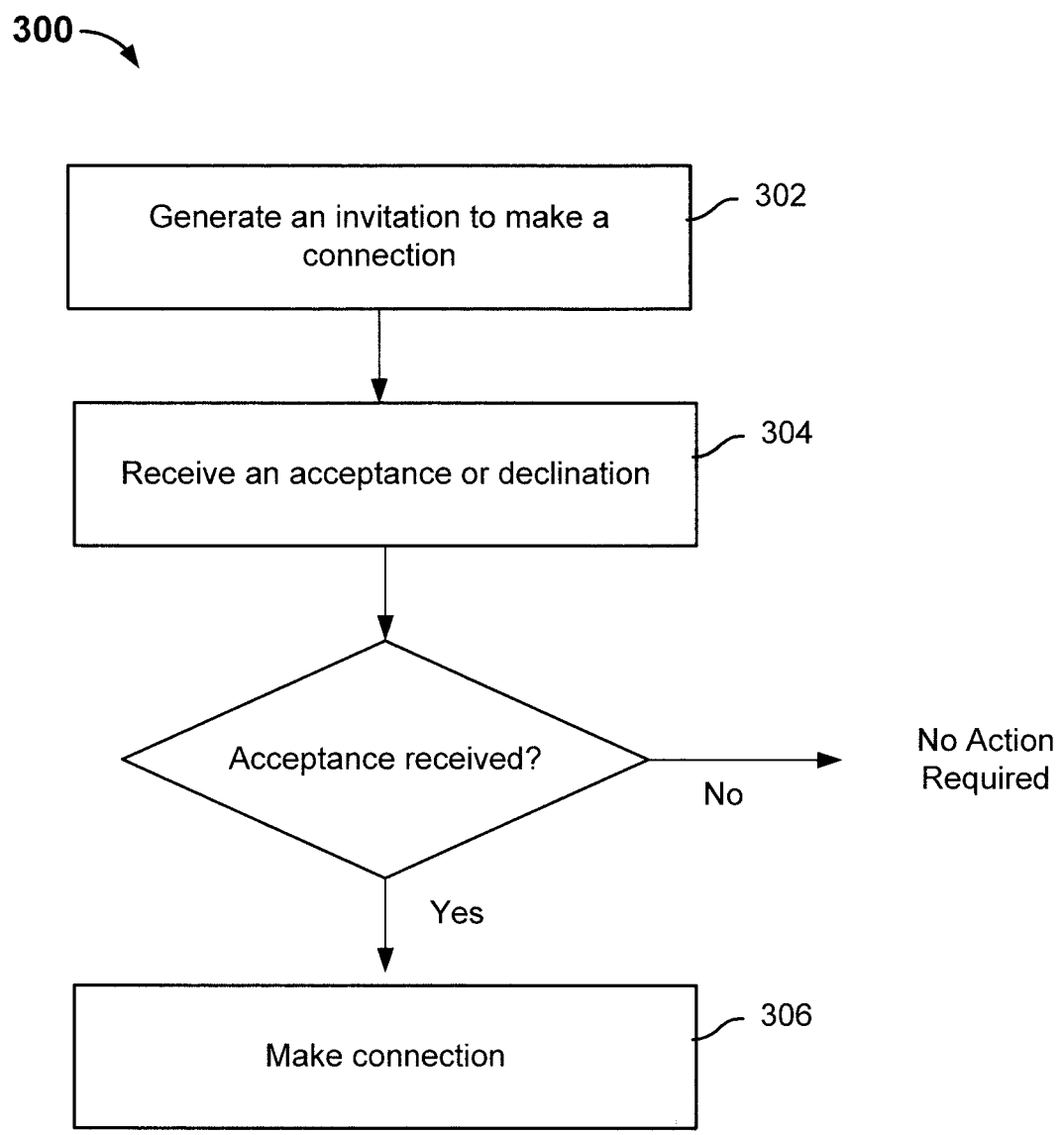
FIG. 3 is a flowchart illustrating an embodiment of a process for connecting a user with potential relatives found in the database.

Upon receiving a notification about another user who is a potential relative, the notified user is allowed to make certain choices about how to interact with the potential relative. FIG. 3 is a flowchart illustrating an embodiment of a process for connecting a user with potential relatives found in the database. The process may be implemented on a relative finder system such as 102, a client system such as 106, or a combination thereof. In this example, it is assumed that it has been determined that Alice and Bob are possibly 4th cousins and that Alice has indicated that she would like to be notified about any potential relatives within 6 generations. In this example, process 300 follows 206 of process 200, where a notification is sent to Alice, indicating that a potential relative has been identified. In some embodiments, the identity of Bob is disclosed to Alice. In some embodiments, the identity of Bob is not disclosed initially to protect Bob's privacy.

Upon receiving the notification, Alice decides that she would like to make a connection with the newly found relative. At 302, an invitation from Alice to Bob inviting Bob to make a connection is generated. In various embodiments, the invitation includes information about how Alice and Bob may be related and any personal information Alice wishes to share such as her own ancestry information. Upon receiving the invitation, Bob can accept the invitation or decline. At 304, an acceptance or a declination is received. If a declination is received, no further action is required. In some embodiments, Alice is notified that a declination has been received. If, however, an acceptance is received, at 306, a connection is made between Alice and Bob. In various embodiments, once a connection is made, the identities and any other sharable personal information (e.g., genetic information, family history, phenotype/traits, etc.) of Alice and Bob are revealed to each other and they may interact with each other. In some embodiments, the connection information is updated in the database.

In some embodiments, a user can discover many potential relatives in the database at once. Additional potential relatives are added as more users join the system and make their genetic information available for the relative finding process. FIGS. 4A-4I are screenshots illustrating user interface examples in connection with process 300. In this example, the relative finder application provides two views to the user: the discovery view and the list view.

Figure 4A:
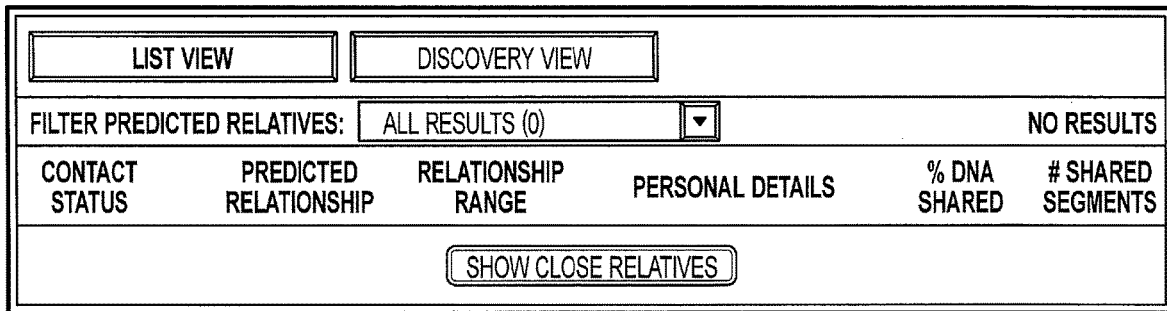
Figure 4B:
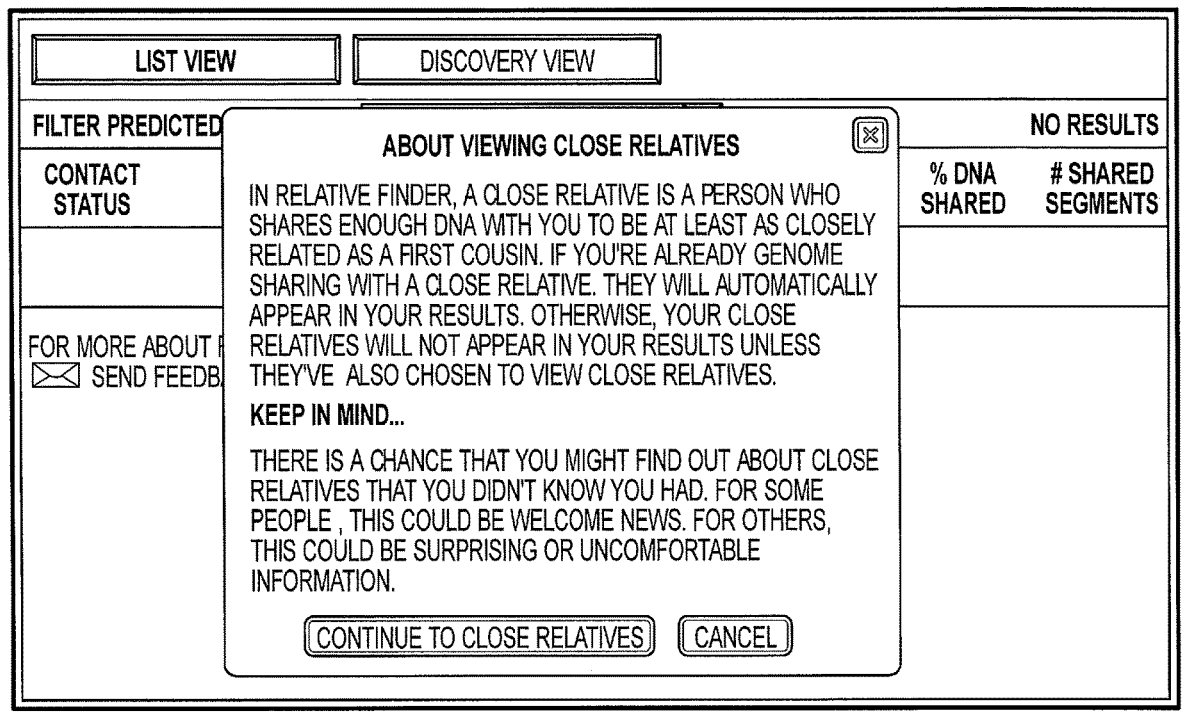

FIG. 4A shows an interface example for the discovery view at the beginning of the process. No relative has been discovered at this point. In this example, a privacy feature is built into the relative finder application so that close relative information will only be displayed if both the user and the close relative have chosen to view close relatives. This is referred to as the "opt in" feature. The user is further presented with a selection button "show close relatives" to indicate that he/she is interested in finding out about close relatives. FIG. 4B shows a message that is displayed when the user selects "show close relatives". The message explains to the user how a close relative is defined. In this case, a close relative is defined as a first cousin or closer. In other words, the system has set a default minimum threshold of three degrees. The message further explains that unless there is already an existing connection between the user and the close relative, any newly discovered potential close relatives will not appear in the results unless the potential close relatives have also chosen to view their close relatives. The message further warns about the possibility of finding out about close relatives the user did not know he/she had. The user has the option to proceed with viewing close relatives or cancel the selection.

FIG. 4C shows the results in the discovery view. In this example, seven potential relatives are found in the database. The predicted relationship, the range of possible relationship, certain personal details a potential relative has made public, the amount of DNA a potential relative shares with the user, and the number of DNA segments the potential relative shares with the user are displayed. The user is presented with a "make contact" selection button for each potential relative.

Figure 4D:

FIG. 4D shows the results in the list view. The potential relatives are sorted according to how close the corresponding predicted relationships are to the user in icon form. The user may select an icon that corresponds to a potential relative and view his/her personal information, the predicted relationship, relationship range, and other additional information. The user can also make contact with the potential relative.

Figure 4E:
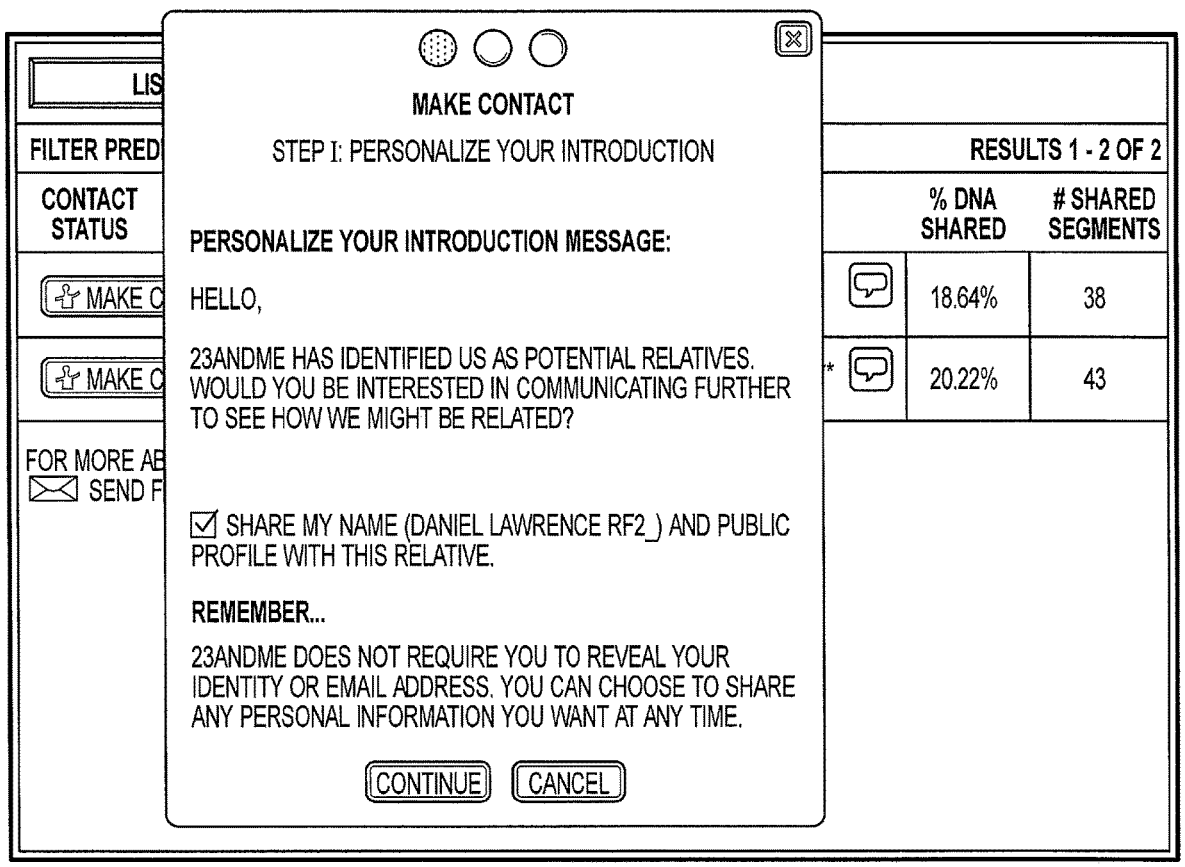
Figure 4F:
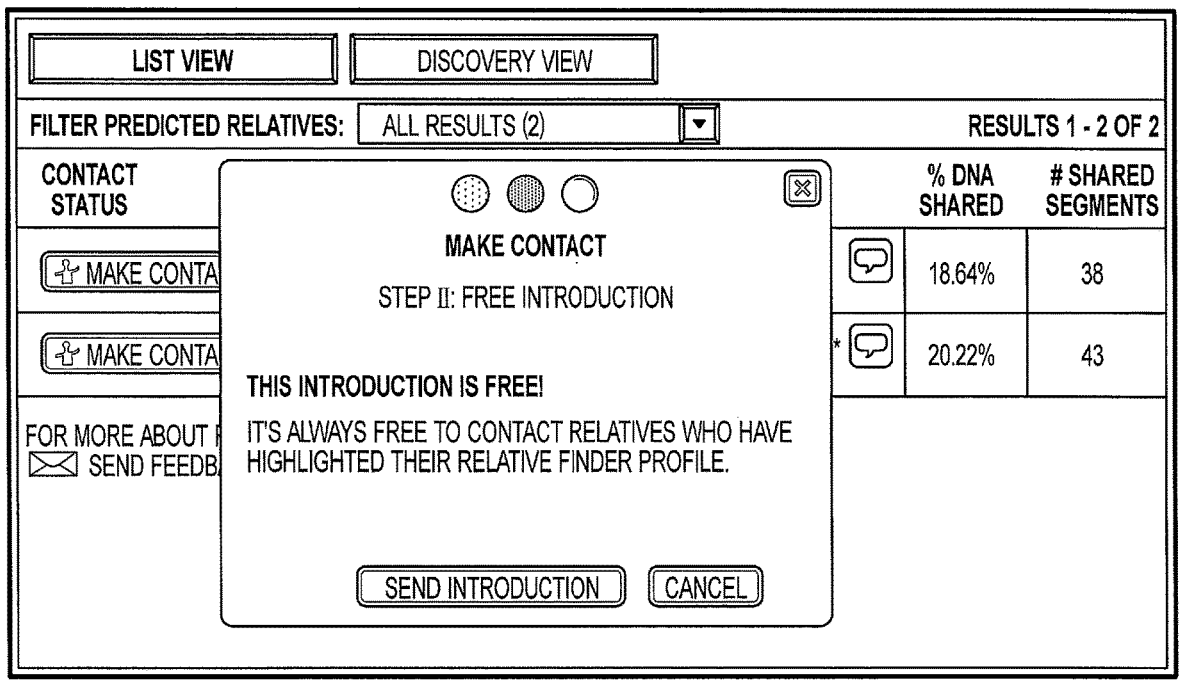
Figure 4G:
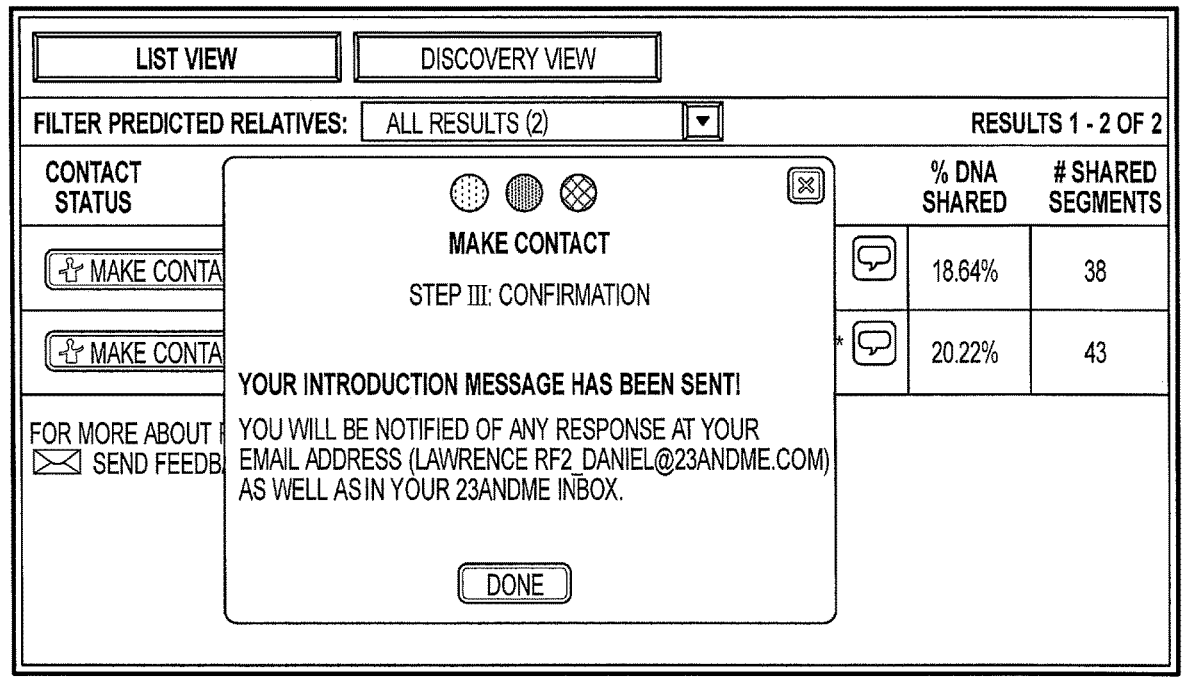

FIGS. 4E-4G show the user interface when the user selects to "make contact" with a potential relative. FIG. 4E shows the first step in making contact, where the user personalizes the introduction message and determine what information the user is willing to share with the potential relative. FIG. 4F shows an optional step in making contact, where the user is told about the cost of using the introduction service. In this case, the introduction is free. FIG. 4G shows the final step, where the introduction message is sent.

FIG. 4H shows the user interface shown to the potential relative upon receiving the introduction message. In this example, the discovery view indicates that a certain user/potential relative has requested to make a contact. The predicted relationship, personal details of the sender, and DNA sharing information are shown to the recipient. The recipient has the option to select "view message" to view the introduction message from the sender.

Figure 4I:
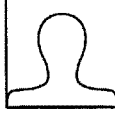

FIG. 4I shows the message as it is displayed to the recipient. In addition to the content of the message, the recipient is given the option to accept or decline the invitation to be in contact with the sender. If the recipient accepts the invitation, the recipient and the sender become connected and may view each other's information and/or interact with each other.

Many other user interfaces can be used in addition to or as alternatives of the ones shown above. For example, in some embodiments, at least some of the potential relatives are displayed in a family tree.

Determining the relationship between two users in the database is now described. In some embodiments, the determination includes comparing the DNA markers (e.g., SNPs) of two users and identifying IBD regions. The standard SNP based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g. triallelic. Other representations are possible.

In this example, A is selected to represent an allele with base A and B represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

Figure 5:
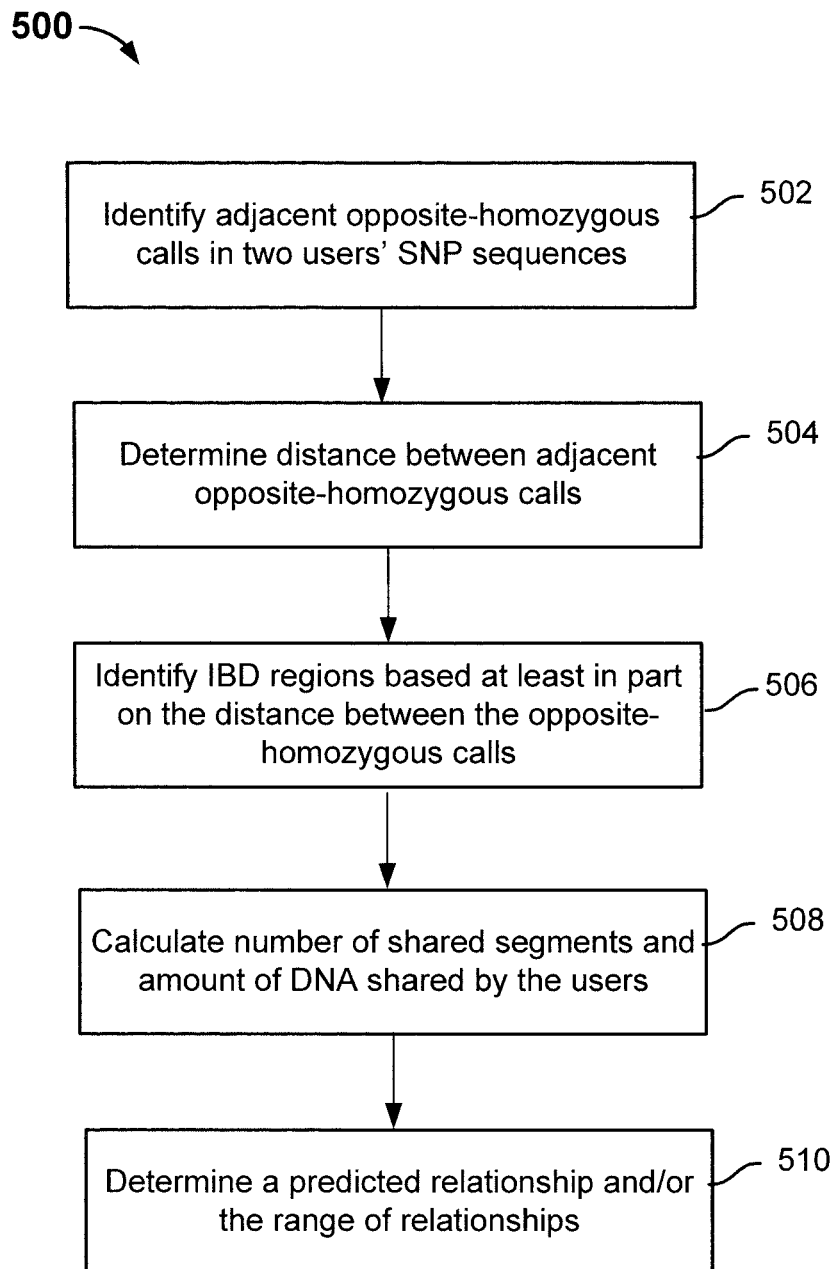
FIG. 5 is a diagram illustrating an embodiment of a process for determining the expected degree of relationship between two users.

FIG. 5 is a diagram illustrating an embodiment of a process for determining the predicted degree of relationship between two users. Process 500 may be implemented on a relative finder system such as 102 and is applicable to unphased data. At 502, consecutive opposite-homozygous calls in the users' SNPs are identified. The consecutive opposite-homozygous calls can be identified by serially comparing individual SNPs in the users' SNP sequences or in parallel using bitwise operations as described below. At 504, the distance between consecutive opposite-homozygous calls is determined. At 506, IBD regions are identified based at least in part on the distance between the opposite-homozygous calls. The distance may be physical distance measured in the number of base pairs or genetic distance accounting for the rate of recombination. For example, in some embodiments, if the genetic distance between the locations of two consecutive opposite-homozygous calls is greater than a threshold of 10 centimorgans (cM), the region between the calls is determined to be an IBD region. This step may be repeated for all the opposite-homozygous calls. A tolerance for genotyping error can be built by allowing some low rate of opposite homozygotes when calculating an IBD segment. In some embodiments, the total number of matching genotype calls is also taken into account when deciding whether the region is IBD. For example, a region may be examined where the distance between consecutive opposite homozygous calls is just below the 10 cM threshold. If a large enough number of genotype calls within that interval match exactly, the interval is deemed IBD.

Figure 6:
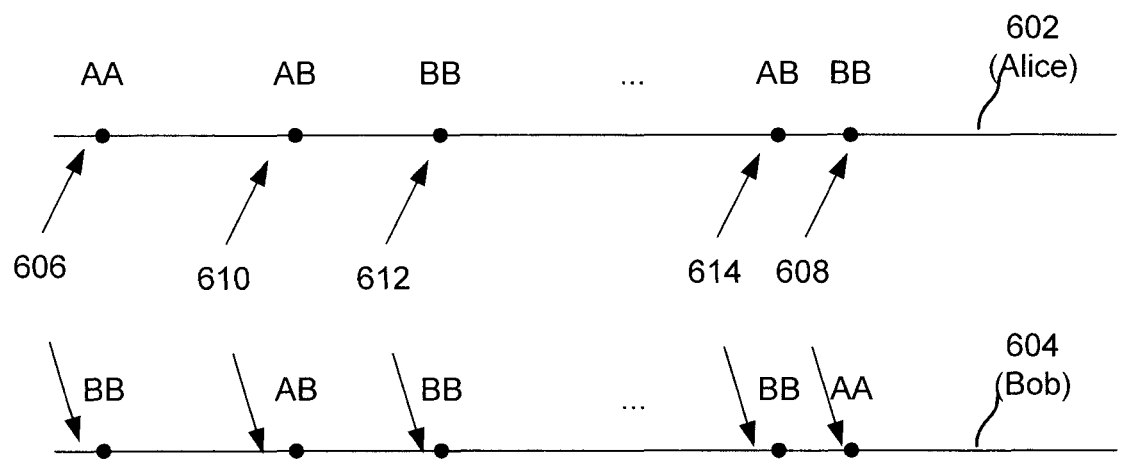
FIG. 6 is a diagram illustrating example DNA data used for IBD identification by process 500.

FIG. 6 is a diagram illustrating example DNA data used for IBD identification by process 500. 602 and 604 correspond to the SNP sequences of Alice and Bob, respectively. At location 606, the alleles of Alice and Bob are opposite-homozygotes, suggesting that the SNP at this location resides in a non-IBD region. Similarly, at location 608, the opposite-homozygotes suggest a non-IBD region. At location 610, however, both pairs of alleles are heterozygotes, suggesting that there is potential for IBD. Similarly, there is potential for IBD at location 612, where both pairs of alleles are identical homozygotes, and at location 614, where Alice's pair of alleles is heterozygous and Bob's is homozygous. If there is no other opposite-homozygote between 606 and 608 and there are a large number of compatible calls between the two locations, it is then likely that the region between 606 and 608 is an IBD region.

Returning to FIG. 5, at 508, the number of shared IBD segments and the amount of DNA shared by the two users are computed based on the IBD. In some embodiments, the longest IBD segment is also determined. In some embodiments, the amount of DNA shared includes the sum of the lengths of IBD regions and/or percentage of DNA shared. The sum is referred to as $IBD_{half}$ or half IBD because the individuals share DNA identical by descent for at least one of the homologous chromosomes. At 510, the predicted relationship between the users, the range of possible relationships, or both, is determined using the $IBD_{half}$ and number of segments, based on the distribution pattern of $IBD_{half}$ and shared segments for different types of relationships. For example, in a first degree parent/child relationship, the individuals have $IBD_{half}$ that is 100% the total length of all the autosomal chromosomes and 22 shared autosomal chromosome segments; in a second degree grandparent/grandchild relationship, the individuals have $IBD_{half}$ that is approximately half the total length of all the autosomal chromosomes and many more shared segments; in each subsequent degree of relationship, the percentage of $IBD_{half}$ of the total length is about 50% of the previous degree. Also, for more distant relationships, in each subsequent degree of relationship, the number of shared segments is approximately half of the previous number.

In various embodiments, the effects of genotyping error are accounted for and corrected. In some embodiments, certain genotyped SNPs are removed from consideration if there are a large number of Mendelian errors when comparing data from known parent/offspring trios. In some embodiments, SNPs that have a high no-call rate or otherwise failed quality control measures during the assay process are removed. In some embodiments, in an IBD segment, an occasional opposite-homozygote is allowed if there is sufficient opposite-homozygotes-free distance (e.g., at least 3 cM and 300 SNPs) surrounding the opposite-homozygote.

Figure 7:
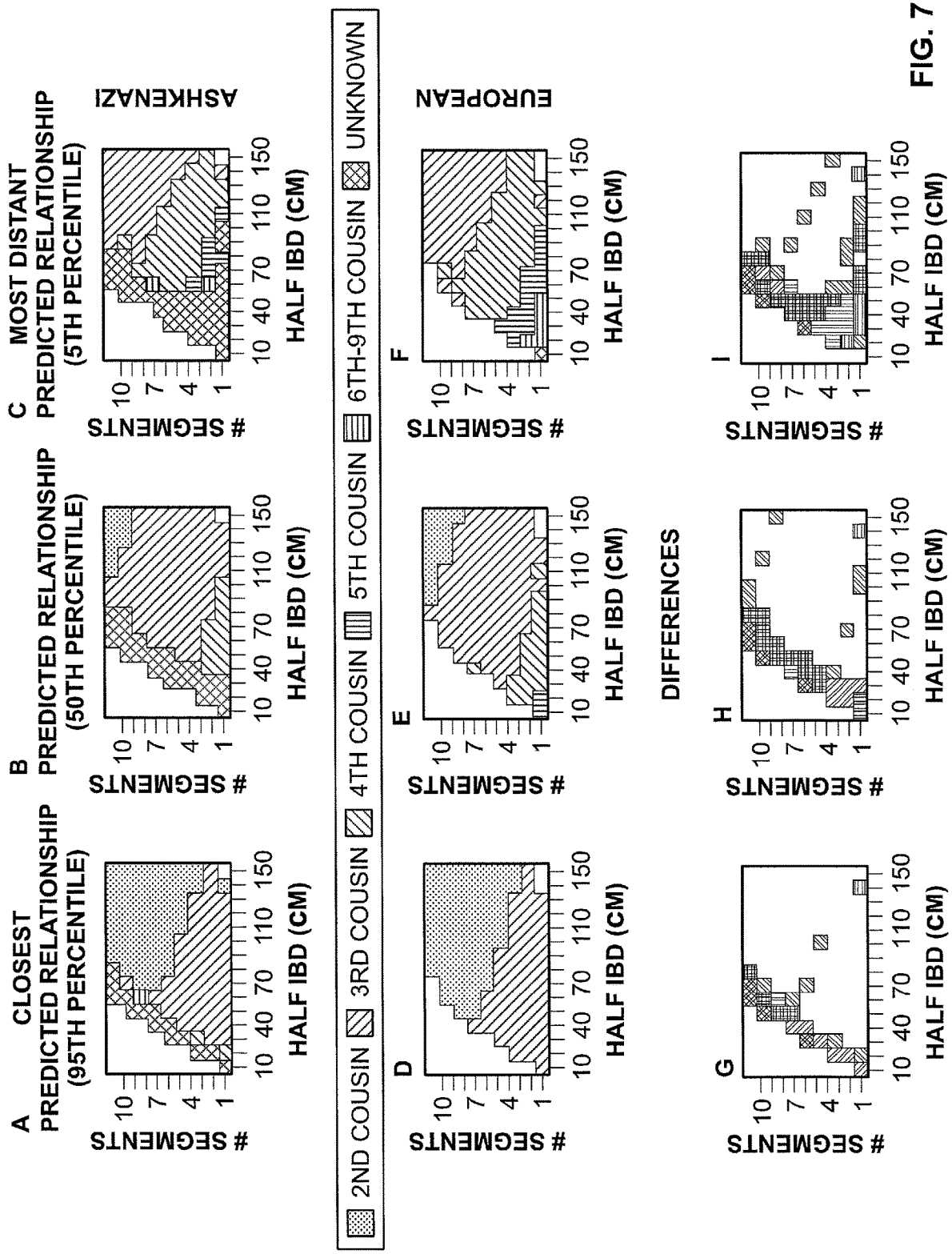
FIG. 7 shows the simulated relationship distribution patterns for different population groups according to one embodiment.

There is a statistical range of possible relationships for the same $IBD_{half}$ and shared segment number. In some embodiments, the distribution patterns are determined empirically based on survey of real populations. Different population groups may exhibit different distribution patterns. For example, the level of homozygosity within endogamous populations is found to be higher than in populations receiving gene flow from other groups. In some embodiments, the bounds of particular relationships are estimated using simulations of IBD using generated family trees. Based at least in part on the distribution patterns, the $IBD_{half}$ and shared number of segments, the degree of relationship between two individuals can be estimated. FIG. 7 shows the simulated relationship distribution patterns for different population groups according to one embodiment. In particular, Ashkenazi Jews and Europeans are two population groups surveyed. In panels A-C, for each combination of $IBD_{half}$ and the number of IBD segments in an Ashkenazi sample group, the 95%, 50% and 5% of obtained nth degree cousinships from 1 million simulated pedigrees are plotted. In panels D-F, for each combination of $IBD_{half}$ and the number of IBD segments in a European sample group, the 95%, 50% and 5% of obtained nth degree cousinships from 1 million simulated pedigrees are plotted. In panels G-I, the differences between Ashkenazi and European distant cousinship for the prior panels are represented. Each nth cousinship category is scaled by the expected number of nth degree cousins given a model of population growth. Simulations are conducted by specifying an extended pedigree and creating simulated genomes for the pedigree by simulating the mating of individuals drawn from a pool of empirical genomes. Pairs of individuals who appear to share $IBD_{half}$ that was not inherited through the specified simulated pedigree are marked as "unknown" in panels A-F. Thus, special distribution patterns can be used to find relatives of users who have indicated that they belong to certain distinctive population groups such as the Ashkenazi.

The amount of IBD sharing is used in some embodiments to identify different population groups. For example, for a given degree of relationship, since Ashkenazi tend to have much more IBD sharing than non-Ashkenazi Europeans, users may be classified as either Ashkenazi or non-Ashkenazi Europeans based on the number and pattern of IBD matches.

In some embodiments, instead of, or in addition to, determining the relationship based on the overall number of IBD segments and percent DNA shared, individual chromosomes are examined to determine the relationship. For example, X chromosome information is received in some embodiments in addition to the autosomal chromosomes. The X chromosomes of the users are also processed to identify IBD. Since one of the X chromosomes in a female user is passed on from her father without recombination, the female inherits one X chromosome from her paternal grandmother and another one from her mother. Thus, the X chromosome undergoes recombination at a slower rate compared to autosomal chromosomes and more distant relationships can be predicted using IBD found on the X chromosomes.

In some embodiments, analyses of mutations within IBD segments can be used to estimate ages of the IBD segments and refine estimates of relationships between users.

In some embodiments, the relationship determined is verified using non-DNA information. For example, the relationship may be checked against the users' family tree information, birth records, or other user information.

Figure 8:
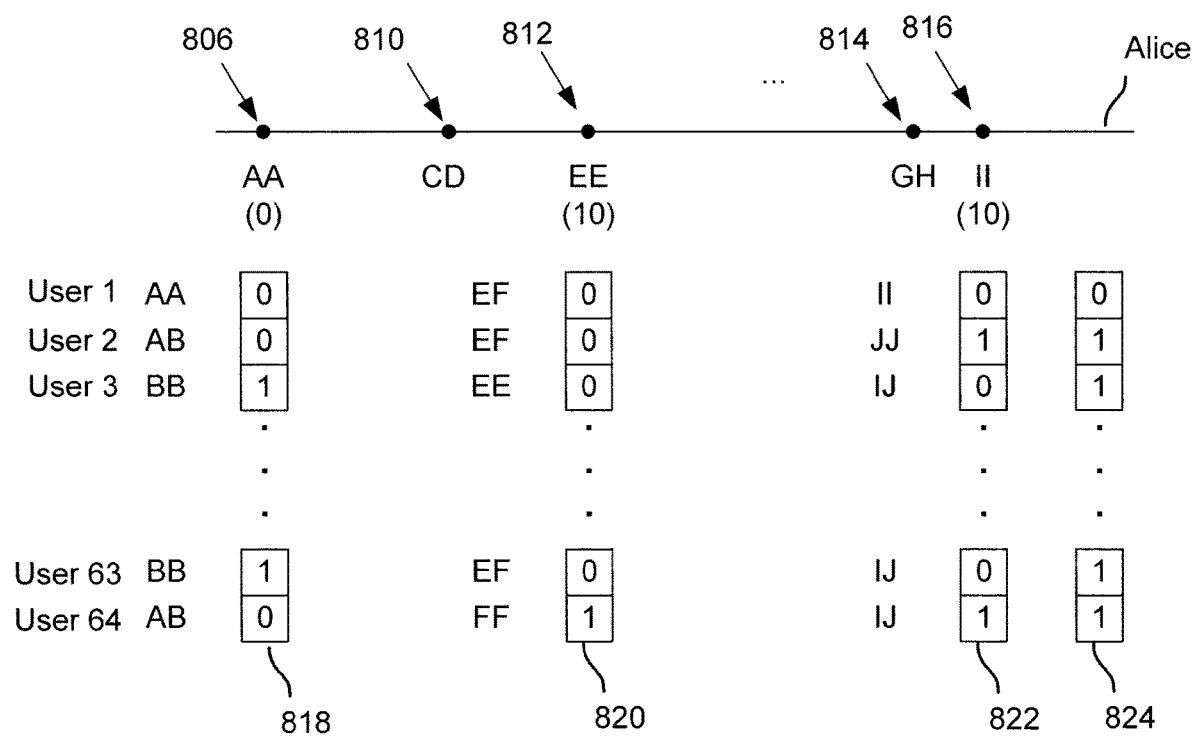
FIG. 8 is a diagram illustrating an embodiment of a highly parallel IBD identification process.

In some embodiments, the efficiency of IBD region identification is improved by comparing a user's DNA information with the DNA information of multiple other users in parallel and using bitwise operations. FIG. 8 is a diagram illustrating an embodiment of a highly parallel IBD identification process. Alice's SNP calls are compared with those of multiple other users. Alice's SNP calls are pre-processed to identify ones that are homozygous. Alice's heterozygous calls are not further processed since they always indicate that there is possibility of IBD with another user. For each SNP call in Alice's genome that is homozygous, the zygosity states in the corresponding SNP calls in the other users are encoded. In this example, compatible calls (e.g., heterozygous calls and same homozygous calls) are encoded as 0 and opposite-homozygous calls are encoded as 1. For example, for homozygous SNP call AA at location 806, opposite-homozygous calls BB are encoded as 1 and compatible calls (AA and AB) are encoded as 0; for homozygous SNP call EE at location 812, opposite-homozygous calls FF are encoded as 1 and compatible calls (EE and EF) are encoded as 0, etc. The encoded representations are stored in arrays such as 818, 820, and 824. In some embodiments, the length of the array is the same as the word length of the processor to achieve greater processing efficiency. For example, in a 64-bit processing system, the array length is set to 64 and the zygosity of 64 users' SNP calls are encoded and stored in the array.

A bitwise operation is performed on the encoded arrays to determine whether a section of DNA such as the section between locations 806 and 810 includes opposite-homozygous calls. In this example, a bitwise OR operation is performed to generate a result array 824. Any user with no opposite-homozygous calls between beginning location 806 and ending location 816 results in an entry value of 0 in array 824. The corresponding DNA segment, therefore, is deemed as an IBD region for such user and Alice. In contrast, users with opposite-homozygotes result in corresponding entry values of 1 in array 824 and they are deemed not to share IBD with Alice in this region. In the example shown, user 1 shares IBD with Alice while other users do not.

In some embodiments, phased data is used instead of unphased data. These data can come directly from assays that produce phased data, or from statistical processing of unphased data. IBD regions are determined by matching the SNP sequences between users. In some embodiments, sequences of SNPs are stored in dictionaries using a hash-table data structure for the ease of comparison. FIG. 9 is a diagram illustrating an example in which phased data is compared to identify IBD. The sequences are split along pre-defined intervals into non-overlapping words. Other embodiments may use overlapping words. Although a preset length of 3 is used for purposes of illustration in the example shown, many implementations may use words of longer lengths (e.g. 100). Also, the length does not have to be the same for every location. In FIG. 9, in Alice's chromosome pair 1, chromosome 902 is represented by words AGT, CTG, CAA, . . . and chromosome 904 is represented by CGA, CAG, TCA, . . . . At each location, the words are stored in a hash table that includes information about a plurality of users to enable constant retrieval of which users carry matching haplotypes. Similar hash tables are constructed for other sequences starting at other locations. To determine whether Bob's chromosome pair 1 shares any IBD with Alice's, Bob's sequences are processed into words at the same locations as Alice's. Thus, Bob's chromosome 906 yields CAT, GAC, CCG, . . . and chromosome 908 yields AAT, CTG, CAA, . . . Every word from Bob's chromosomes is then looked up in the corresponding hash table to check whether any other users have the same word at that location in their genomes. In the example shown, the second and third words of chromosome 908 match second and third words of Alice's chromosome 902. This indicates that SNP sequence CTGCAA is present in both chromosomes and suggests the possibility of IBD sharing. If enough matching words are present in close proximity to each other, the region would be deemed IBD.

In some embodiments, relative relationships found using the techniques described above are used to infer characteristics about the users that are related to each other. In some embodiments, the inferred characteristic is based on non-genetic information pertaining to the related users. For example, if a user is found to have a number of relatives that belong to a particular population group, then an inference is made that the user may also belong to the same population group. In some embodiments, genetic information is used to infer characteristics, in particular characteristics specific to shared IBD segments of the related users. Assume, for example, that Alice has sequenced her entire genome but her relatives in the system have only genotyped SNP data. If Alice's genome sequence indicates that she may have inherited a disease gene, then, with Alice's permission, Alice's relatives who have shared IBD with Alice in the same region that includes the disease gene may be notified that they are at risk for the same disease.

Although the foregoing embodiments have been described in some detail for purposes of clarity of understanding, the invention is not limited to the details provided.

There are many alternative ways of implementing the invention. The disclosed embodiments are illustrative and not restrictive.

What is claimed is:

1. A computer-implemented method comprising:
   receiving, by a computing system and from a user, an opt-in election to consent to being presented with information about potential familial relatives among a plurality of users in a familial relative finder database, wherein the familial relative finder database comprises recombinable deoxyribonucleic acid (DNA) sequence information of the plurality of users, including that of the user;
   determining, by the computing system and from identical-by-descent (IBD) segments from the recombinable DNA of the user and the recombinable DNA of the plurality of users, familial relative relationships between the user and each of a subset of users from the plurality of users; and
   providing, by the computing system and for display on a client device of the user, a representation of a graphical user interface indicating the familial relative relationships between the user and each of the subset of users in tabular form, wherein each entry in the tabular form displays, for the user and a particular user of the subset of users, a predicted familial relative relationship and a percent of DNA shared.

2. The computer-implemented method of claim 1, wherein an entry in the tabular form displays an icon selectable by way of the graphical user interface that facilitates making contact between the user and a second user to which the entry applies.

3. The computer-implemented method of claim 2, further comprising:
   receiving, from the client device, an indication that the user has selected the icon; and
   in response to receiving the indication, providing, for display on the client device, a representation of a second graphical user interface that prompts the user to enter a personalized introduction message and to select personal information that the user is willing to share with the second user.

4. The computer-implemented method of claim 3, further comprising:
   receiving, from the client device, the personalized introduction message or selection of the personal information; and
   in response to receiving the personalized introduction message or selection of the personal information, transmitting an invitation to connect to the second user on behalf of the user.

5. The computer-implemented method of claim 4, wherein the second user has opted-in to being presented with information about potential familial relatives among the plurality of users.

6. The computer-implemented method of claim 4, further comprising:
   receiving, from a second client device associated with the second user, an acceptance of the invitation to connect; and
   in response to receiving the acceptance of the invitation to connect, updating the familial relative finder database to indicate that the user and the second user are connected.

7. The computer-implemented method of claim 6, further comprising:
   based on the user and the second user being connected, revealing identifies, genetic information, and existing familial relative relationships of the user and the second user to one another.

8. The computer-implemented method of claim 6, further comprising:
   based on the user and the second user being connected, inferring an additional familial relative relationship between the user and a third user from an existing familial relative relationship between the second user and the third user.

9. The computer-implemented method of claim 1, further comprising:
   receiving, from the user, a number of generations as a threshold relationship value, wherein each of the subset of users has a respective common ancestor with the user that is no more than the number of generations from the user.

10. The computer-implemented method of claim 1, wherein determining the familial relative relationships between the user and each of the subset of users comprises determining common patterns of nucleotides between the user and each of the subset of users.

11. The computer-implemented method of claim 10, wherein the common patterns of nucleotides between the user and each of the subset of users are common lengths of recombinable DNA of the user and recombinable DNA of at least one of the subset of users exceeding a predetermined threshold.

12. The computer-implemented method of claim 1, wherein the entries in the tabular form are sorted according to closeness of the predicted familial relative relationships with the user.

13. The computer-implemented method of claim 1, wherein the entries in the tabular form are anonymized to hide identities of the subset of users.

14. The computer-implemented method of claim 1, wherein each of the subset of users has opted-in to being presented with information about potential familial relatives among the plurality of users.

15. The computer-implemented method of claim 1, wherein each entry in the tabular form also displays, for the user and the particular user of the subset of users, a number of IBD segments shared.

16. A non-transitory computer-readable medium, having stored thereon program instructions that, upon execution by a computing device, cause the computing device to perform operations comprising:
   receiving, from a user, an opt-in election to consent to being presented with information about potential familial relatives among a plurality of users in a familial relative finder database, wherein the familial relative finder database comprises recombinable deoxyribonucleic acid (DNA) sequence information of the plurality of users, including that of the user;
   determining, from identical-by-descent (IBD) segments from the recombinable DNA of the user and the recombinable DNA of the plurality of users, familial relative relationships between the user and each of a subset of users from the plurality of users; and
   providing, for display on a client device of the user, a representation of a graphical user interface indicating the familial relative relationships between the user and each of the subset of users in tabular form, wherein each entry in the tabular form displays, for the user and a particular user of the subset of users, a predicted familial relative relationship and a percent of DNA shared.

17. The non-transitory computer-readable medium of claim 16, wherein an entry in the tabular form displays an icon selectable by way of the graphical user interface that facilitates making contact between the user and a second user to which the entry applies.

18. The non-transitory computer-readable medium of claim 17, further comprising:
receiving, from the client device, an indication that the user has selected the icon; and
in response to receiving the indication, providing, for display on the client device, a representation of a second graphical user interface that prompts the user to enter a personalized introduction message and to select personal information that the user is willing to share with the second user.

19. The non-transitory computer-readable medium of claim 18, further comprising:
receiving, from the client device, the personalized introduction message or selection of the personal information; and
in response to receiving the personalized introduction message or selection of the personal information, transmitting an invitation to connect to the second user on behalf of the user.

20. A computing system comprising:
one or more processors; and
memory containing instructions that, when executed by the one or more processors, cause the computing system to perform operations comprising:
receiving, from a user, an opt-in election to consent to being presented with information about potential familial relatives among a plurality of users in a familial relative finder database, wherein the familial relative finder database comprises recombinable deoxyribonucleic acid (DNA) sequence information of the plurality of users, including that of the user;
determining, from identical-by-descent (IBD) segments from the recombinable DNA of the user and the recombinable DNA of the plurality of users, familial relative relationships between the user and each of a subset of users from the plurality of users; and
providing, for display on a client device of the user, a representation of a graphical user interface indicating the familial relative relationships between the user and each of the subset of users in tabular form, wherein each entry in the tabular form displays, for the user and a particular user of the subset of users, a predicted familial relative relationship and a percent of DNA shared.

* * * * *